US012661121B2

(12) United States Patent
Berger et al.

(10) Patent No.: US 12,661,121 B2
(45) Date of Patent: Jun. 23, 2026

(54) BODY LUMEN WALL INVAGINATION

(71) Applicant: Append Medical Ltd., Or Yehuda (IL)

(72) Inventors: Zachi Berger, Nes Ziona (IL); Shay Raviv, Zur Hadassa (IL); Oded Meiri, Moshav Ram-On (IL); Gal Atarot, Kfar Saba (IL); Gal Yamin, Givatayim (IL); Liz Zinger, Kiryat Ono (IL); Nadav Agian, Kfar Yona (IL)

(73) Assignee: Append Medical Ltd., Or Yehuda (IL)

( * ) Notice: Subject to any disclaimer, the term of this patent is extended or adjusted under 35 U.S.C. 154(b) by 82 days.

(21) Appl. No.: 18/580,631

(22) PCT Filed: Jul. 19, 2022

(86) PCT No.: PCT/IL2022/050778
§ 371 (c)(1),
(2) Date: Jan. 19, 2024

(87) PCT Pub. No.: WO2023/002482
PCT Pub. Date: Jan. 26, 2023

(65) Prior Publication Data
US 2025/0072900 A1 Mar. 6, 2025

Related U.S. Application Data

(60) Provisional application No. 63/223,137, filed on Jul. 19, 2021.

(51) Int. Cl.
*A61B 17/12* (2006.01)
*A61B 17/00* (2006.01)
(52) U.S. Cl.
CPC ................... *A61B 17/12013* (2013.01); *A61B 2017/00566* (2013.01); *A61B 2017/00778* (2013.01)

(58) Field of Classification Search
CPC .............. A61B 17/12; A61B 17/12013; A61B 17/12027; A61B 17/12031;
(Continued)

(56) References Cited

U.S. PATENT DOCUMENTS

| | | | |
|---|---|---|---|
| 6,383,198 B1 * | 5/2002 | Hamilton | A61B 17/22031 606/115 |
| 2002/0058856 A1 * | 5/2002 | Peng | A61B 17/02 600/201 |

(Continued)

FOREIGN PATENT DOCUMENTS

| | | |
|---|---|---|
| WO | WO 2021/001830 | 1/2021 |
| WO | WO 2023/002482 | 1/2023 |

OTHER PUBLICATIONS

Invitation to Pay Additional Fees, Communication Relating to the Result of the Partial International Search and the Provisional Opinion Dated Mar. 13, 2025 From the International Searching Authority Re. Application No. 22845565.5 (19 Pages).
(Continued)

*Primary Examiner* — Tuan V Nguyen

(57) ABSTRACT

A method for left atrial appendage (LAA) invagination, including:
convexing a portion of the LAA wall into the LAA, wherein the convexing includes convexing the LAA wall portion by applying suction from a collapsible suction cup contacting the LAA wall on the LAA wall portion;
grasping the convexed LAA wall portion within the LAA, following the convexing; invaginating the LAA at least partly into the left atria (LA) using the convexed LAA portion;
wherein the grasping includes controllably collapsing the collapsible suction cup on the convexed LAA portion with a force sufficient to hold the convexed LAA portion during the invaginating.

14 Claims, 25 Drawing Sheets

(58) Field of Classification Search
    CPC .... A61B 17/12122; A61B 2017/00561; A61B
                        2017/00566; A61B 2017/00778
    See application file for complete search history.

(56)                    References Cited

U.S. PATENT DOCUMENTS

| | | |
|---|---|---|
| 2010/0145361 A1 | 6/2010 | Francischelli et al. |
| 2014/0171733 A1 | 6/2014 | Sternik |
| 2016/0022273 A1 | 1/2016 | Kassab |
| 2019/0298382 A1 | 10/2019 | Fung |
| 2020/0100796 A1 | 4/2020 | Berger et al. |
| 2021/0186547 A1* | 6/2021 | Kassab ............... A61M 25/008 |
| 2022/0354472 A1 | 11/2022 | Berger et al. |

OTHER PUBLICATIONS

International Preliminary Report on Patentability Dated Feb. 1,
2024 From the International Bureau of WIPO Re. Application No.
PCT/IL2022/050778 (12 Pages).
International Search Report and the Written Opinion Dated Oct. 31,
2022 From the International Searching Authority Re. Application
No. PCT/II.2022/050778. (18 Pages).
Supplementary European Search Report and the European Search
Opinion Dated Jun. 25, 2025 From the European Patent Office Re.
Application No. 22845565.5 (21 Pages).

\* cited by examiner

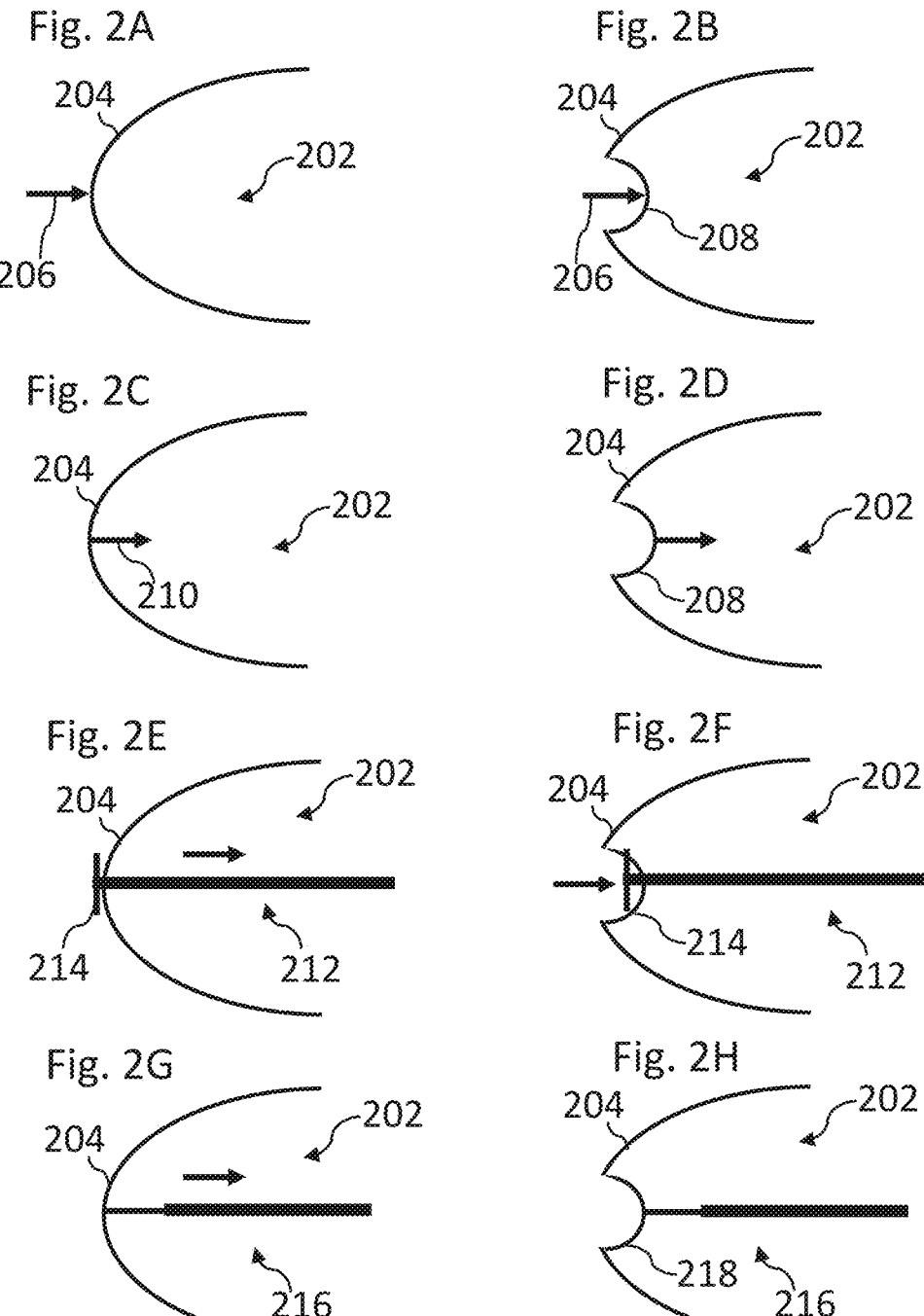

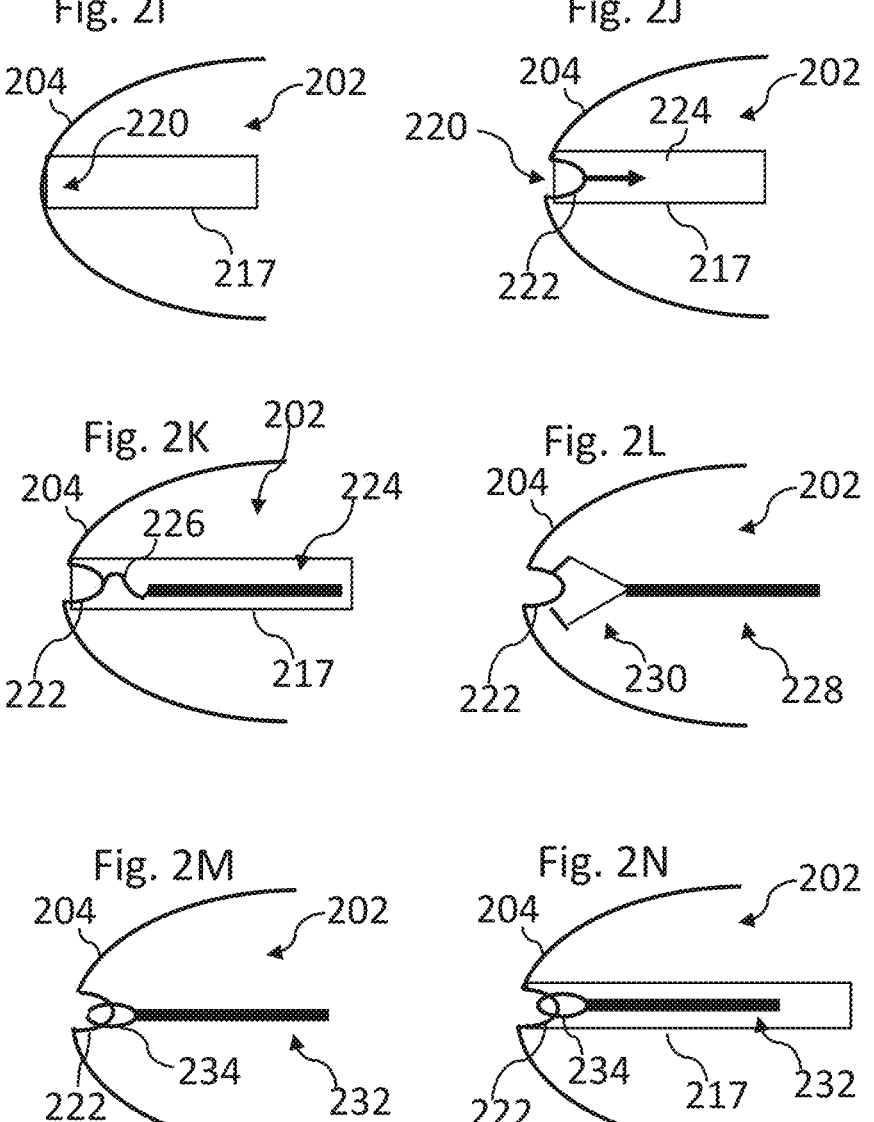

Fig. 8D
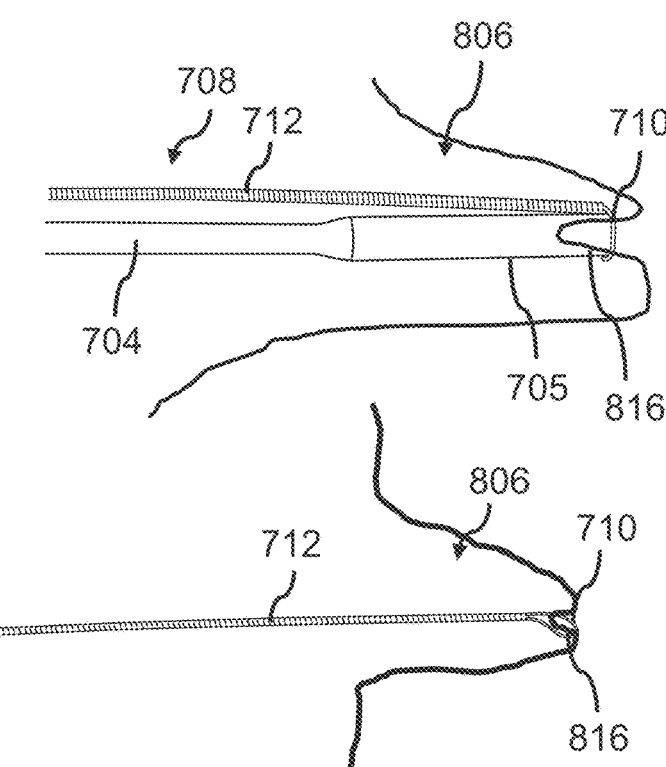
Fig. 8E
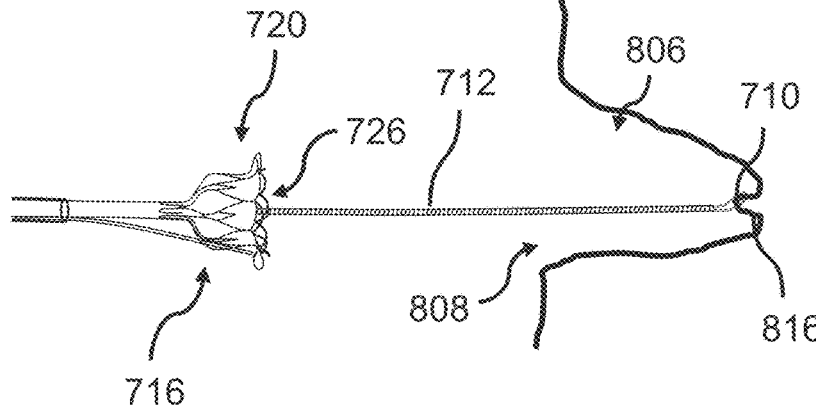
Fig. 8F
Fig. 8G
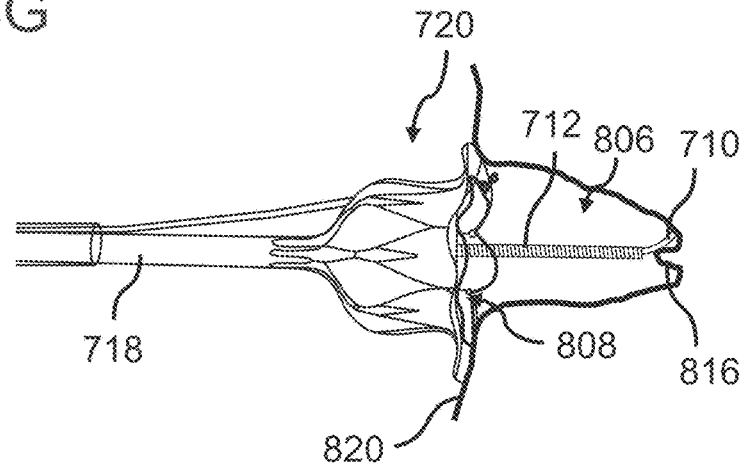

Fig. 10A
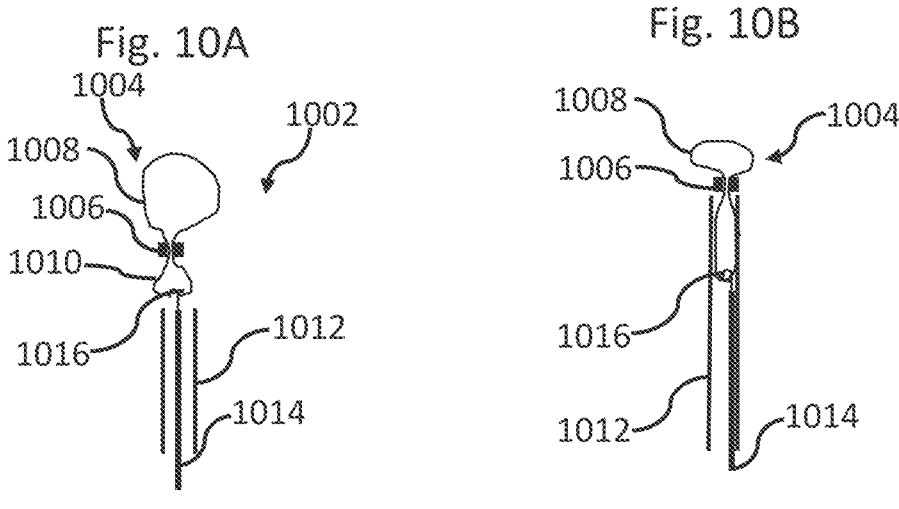
Fig. 10B
Fig. 10C
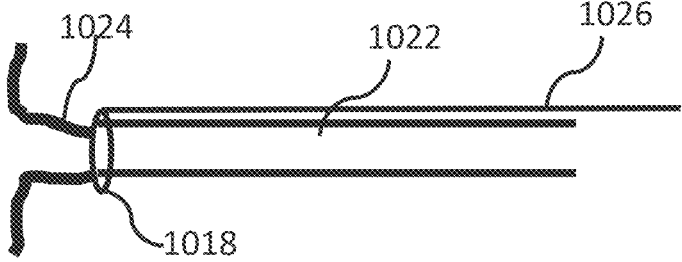
Fig. 10D
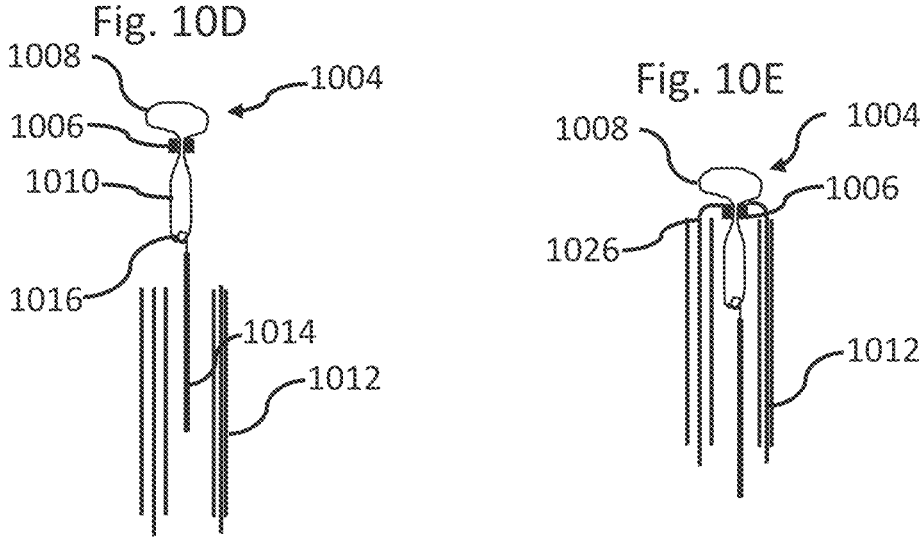
Fig. 10E

Fig. 11A
Fig. 11B
Fig. 11C
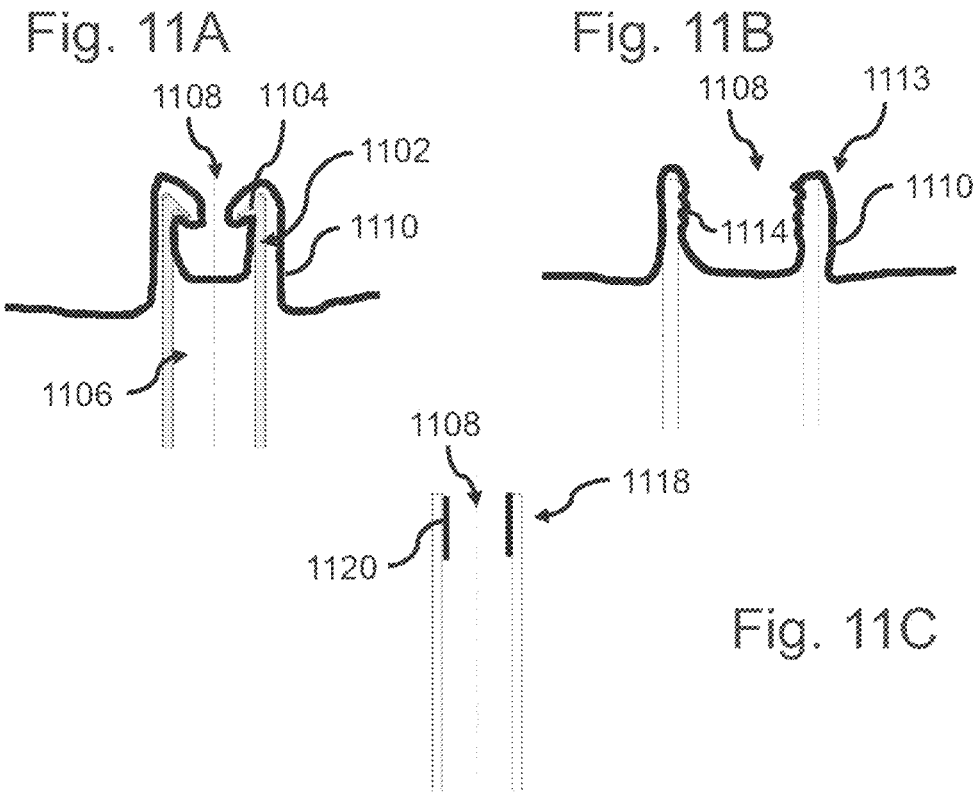
Fig. 11D
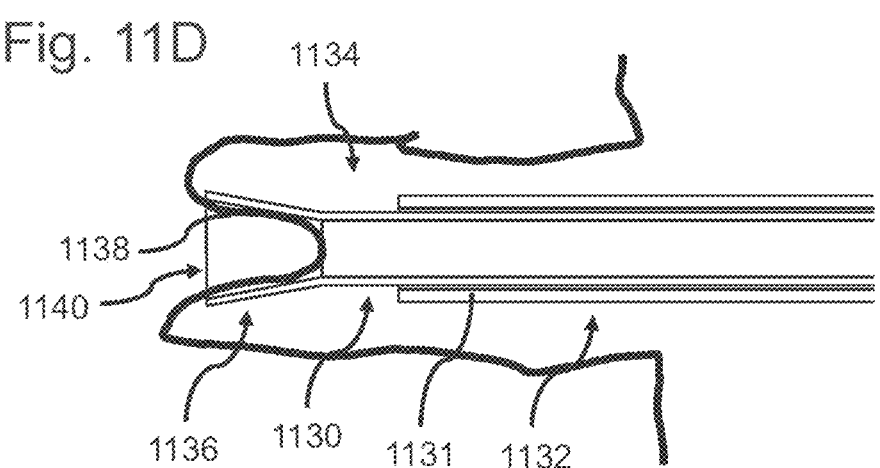
Fig. 12
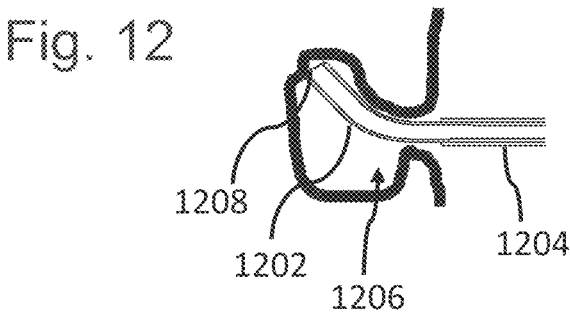

Fig. 17C
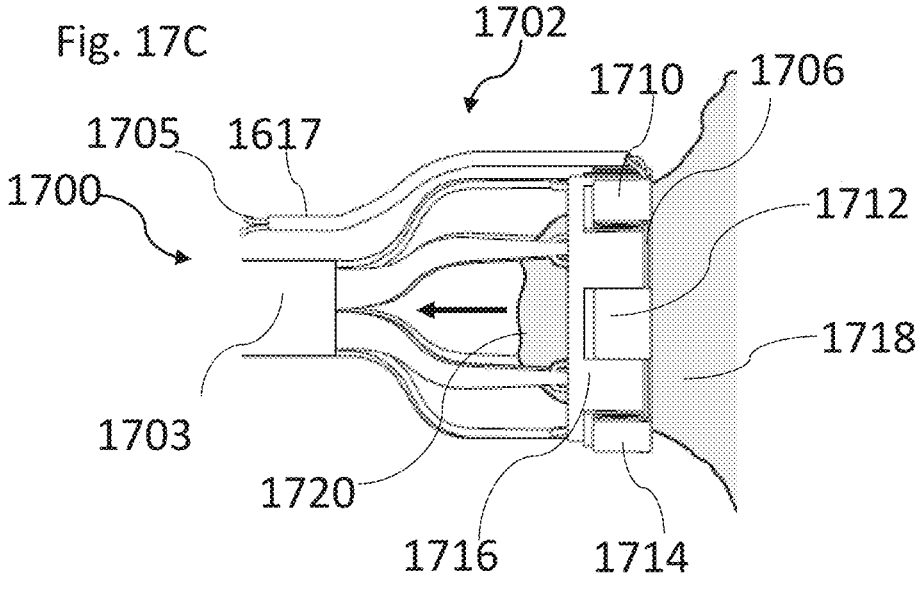
Fig. 17D
Fig. 17E
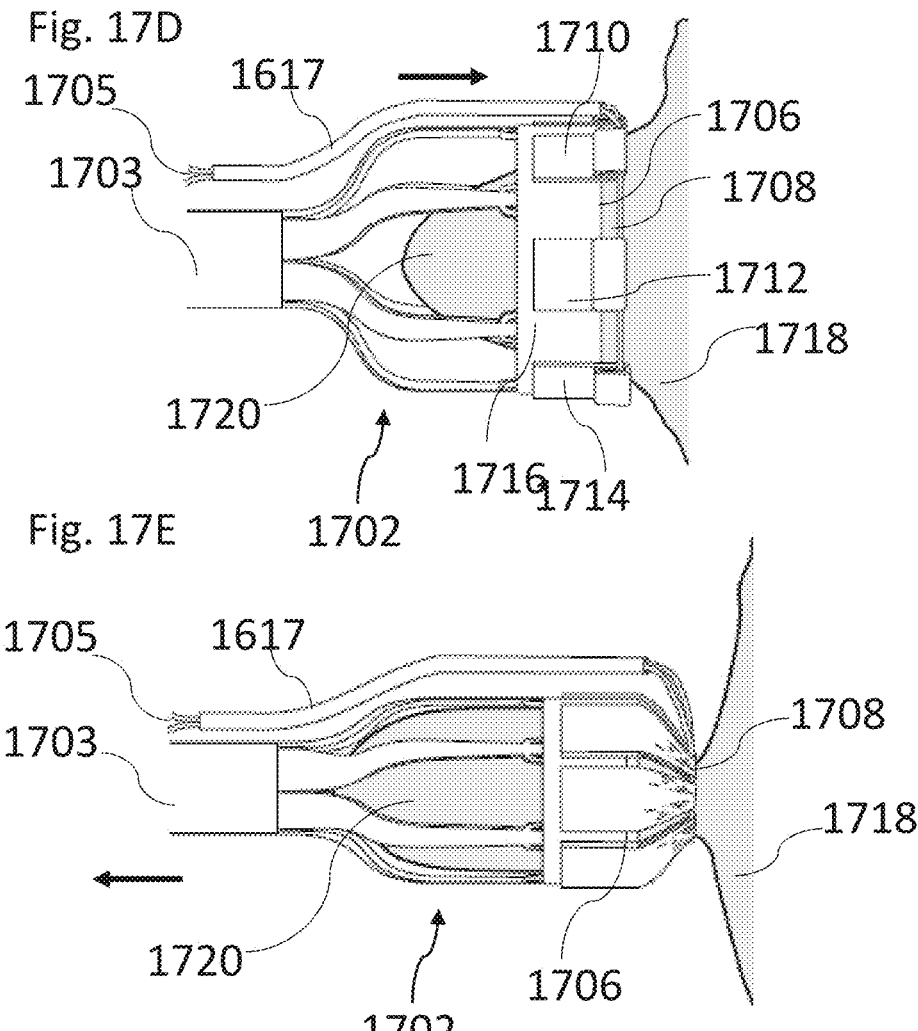

BODY LUMEN WALL INVAGINATION

RELATED APPLICATION(S) APPLICATIONS

This application is a National Phase of PCT Patent Application No. PCT/IL2022/050778 having International filing date of Jul. 19, 2022, which claims the benefit of priority under 35 USC § 119 (e) of U.S. Provisional Patent Application No. 63/223,137 filed on Jul. 19, 2021. The contents of the above applications are all incorporated by reference as if fully set forth herein in their entirety.

PCT Patent Application No. PCT/IL2022/050778 is also related to international patent application no. PCT/IL2020/050737, having publication no. WO2021/001830, filed on Jul. 2, 2020, the contents of which are all incorporated by reference as if fully set forth herein in its entirety.

FIELD AND BACKGROUND OF THE INVENTION

The present invention, in some embodiments thereof, relates to closure of a body lumen and, more particularly, but not exclusively, to closure of a left atrial appendage (LAA) within a heart.

SUMMARY OF THE INVENTION

The following describes some examples of embodiments of the invention (an embodiment may include features from more than one example and/or fewer than all features of an example):

Example 1. A method for left atrial appendage (LAA) invagination, comprising:

convexing a portion of the LAA wall into the LAA;

grasping said convexed LAA wall portion within the LAA;

invaginating said LAA at least partly into the left atria (LA) using said convexed LAA portion.

Example 2. A method according to example 1, wherein said convexing comprises convexing said LAA wall portion to a distance of up to 2 cm into the LAA.

Example 3. A method according to any one of examples 1 or 2, wherein said convexing comprises applying force on an inner surface of said LAA wall from within the LAA, which is sufficient to convex said LAA wall portion into the LAA.

Example 4. A method according to example 3, wherein said applied force is atraumatic to the LAA wall.

Example 5. A method according to any one of the previous examples, wherein said convexing and said grasping are separated in time.

Example 6. A method according to any one of the previous examples, wherein said convexing comprises applying a first force on a region of said LAA wall which is sufficient to convex said LAA wall portion, and wherein said grasping comprises applying a second force on a smaller portion of said region to grasp said convexed LAA wall portion.

Example 7. A method according to any one of the previous examples, wherein said convexing comprises convexing said LAA wall portion by applying suction from a suction tube on said LAA wall portion, and wherein said grasping comprises grasping said convexed LAA portion using a tissue grasper that applies a force on a small area of said convexed LAA wall portion.

Example 8. A method according to example 1, comprising introducing a LAA invaginator into the LAA, wherein said convexing comprises convexing said LAA wall portion into a lumen of the LAA invaginator, and wherein said grasping comprises holding said convexed LAA wall by applying force on the convexed LAA portion positioned within said LAA invaginator lumen.

Example 9. A method according to example 8, wherein said holding comprises holding said convexed LAA wall by applying vacuum by said LAA invaginator on said convexed LAA wall within said LAA invaginator lumen.

Example 10. A method according to any one of examples 1 to 8, wherein said grasping comprises tightening a loop around said convexed LAA wall portion.

Example 11. A method according to example 10, wherein said tightening comprises reversibly tightening said loop around said convexed LAA wall portion, and wherein said method comprises releasing said loop from said convexed LAA after said LAA is invaginated into said LA.

Example 12. A method according to any one of the previous examples, wherein said convexing comprises applying suction force on said LAA wall to convex said LAA wall portion into said LAA.

Example 13. A method according to example 12, wherein said suction force is applied with a pressure level in a range of 50 mmHG-760 mmHG.

Example 14. A method according to any one of examples 1 or 2, wherein said convexing comprises penetrating at least partly into the LAA wall, and convexing said LAA wall portion by applying force from within the LAA wall or on an outer surface of the LAA wall located outside the heart, towards the LAA lumen.

Example 15. A method according to any one of examples 1 or 2, wherein said convexing comprises applying force from outside the heart on an outer surface of said LAA wall towards the LAA lumen.

Example 16. A method according to any one of the previous examples, wherein said invaginating comprises invaginating said LAA entirely into the LA.

Example 17. A method according to any one of the previous examples, wherein said invaginating comprises invaginating said LAA at least partly through a LAA opening in the LA.

Example 18. A method according to any one of the previous examples, comprising closing said invaginated LAA.

Example 19. A method according to example 18, wherein said closing comprises placing a ligator in contact with the invaginated LAA.

Example 20. A method according to example 19, wherein said closing comprises tightening a loop of said ligator around said invaginated LAA.

Example 21. A method according to example 20, wherein said loop comprises a lasso suture or an elastic band.

Example 22. A method according to example 19, wherein said closing comprises placing a clip around the invaginated LAA.

Example 23. A method according to example 18, wherein said closing comprises irreversibly closing the invaginated LAA.

Example 24. A method according to any one of the previous examples, comprises sealing a LAA opening in the LA from passage of blood clots, particles and/or debris from the LAA into the LA prior to said convexing or prior to said invaginating.

Example 25. A method according to any one of the previous examples, wherein said invaginating comprises reshaping of the invaginated LAA.

Example 26. A LAA invaginating device, comprising:

a catheter having a proximal opening and a distal opening, wherein said catheter is shaped and sized to be introduced into the LA;

an elongated tubular body having a distal end with a distal opening and a proximal opening, wherein said elongated tubular body is shaped and sized to move within said catheter, to extend at least partly from the catheter distal opening into the LAA, and to contact a wall of said LAA with said elongated tubular body distal opening, wherein said elongated tubular body is configured to apply force on said LAA wall which is sufficient to convex a portion of said LAA wall into said elongated tubular body through said elongated tubular body distal opening;

at least one tissue grasper associated with said elongated tubular body, wherein said at least one tissue grasper is configured to move within said catheter and to hold said convexed portion of the LAA wall positioned within the elongated body;

wherein retraction of said at least one tissue grasper into said catheter while holding said convexed LAA portion, invaginates said LAA at least partly into said LA.

Example 27. A device according to example 26, wherein said elongated tubular body comprises at least one connector for connecting said elongated tubular body proximal opening to a vacuum source, and wherein said elongated tubular body is configured to apply suction on said LAA wall.

Example 28. A device according to any one of examples 26 or 27, wherein said distal end of said elongated tubular body, configured to contact said LAA wall is soft and/or flexible.

Example 29. A device according to any one of examples 26 to 28, wherein said at least one tissue grasper is configured to move over said elongated tubular body and said elongated tubular body distal end.

Example 30. A device according to example 29, wherein said at least one tissue grasper comprises a loop, wherein said loop is configured to move between a closed state in which said loop is tightened, and an expanded state.

Example 31. A device according to any one of examples 26 or 27, wherein said elongated tubular body terminates with a suction cup at said elongated tubular body distal end, and wherein said suction cup is configured to be placed in contact with said LAA wall.

Example 32. A device according to example 31 wherein a width of an opening of said suction cup configured to be placed in contact with said LAA wall is in a range of 3 mm-10 mm.

Example 33. A device according to any one of examples 31 or 32, wherein said suction cup is an expandable suction cup configured to expand when said elongated tubular body extends out from the catheter, and to collapse within said catheter.

Example 34. A device according to any one of examples 31 to 33, wherein at least a portion of said suction cup configured to be placed in contact with the LAA wall is soft and/or flexible.

Example 35. A device according to any one of examples 31 to 34, wherein said at least one tissue grasper comprises a loop, wherein said loop is configured to move between a closed state in which said loop is tightened, and an expanded state.

Example 36. A device according to example 35, wherein a maximal width of said loop in an expanded state is in a range of 5 mm-15 mm.

Example 37. A device according to any one of examples 35 or 36, wherein said loop in an expanded state is coupled to said expanded portion and is configured to detach from said expanded portion when tightened.

Example 38. A device according to any one of examples 35 or 36, wherein said at least one tissue grasper comprises a rod coupled to said loop, wherein said rod is configured to move said loop over said elongated tubular body and said expanded portion.

Example 39. A device according to example 38, wherein said loop moves between said closed state and said expanded state when the rod rotates and/or axially moves.

Example 40. A device according to example 38, wherein said loop is connected to a wire passing within said rod, and wherein said loop is configured to move between said closed state and said expanded state when said wire is moved.

Example 41. A device according to any one of examples 26 to 28, wherein said at least one tissue grasper comprises an elongated body terminating with a collapsible distal cup, wherein said collapsible distal cup is configured to controllably collapse over said convex portion with a force sufficient to hold said convex portion while said at least one tissue grasper is retracted into the catheter.

Example 42. A device according to example 41, wherein said collapsible distal cup comprises a plurality of movable spaced-apart extensions movably coupled to said elongated body.

Example 43. A device according to example 42, wherein said collapsible distal cup comprises a sheet material connected to at least some of said plurality of movable spaced-apart extensions, defining an inner lumen and a distal opening of said collapsible distal cup.

Example 44. A device according to any one of examples 26 to 28, wherein said at least one tissue grasper comprises an elongated body terminating with a plurality of extensions movably coupled to said elongated body around said distal opening of said elongated tubular body, wherein said plurality of extensions are configured to move between a tilted open state where each of said plurality of extensions is tilted away from a longitudinal axis of said elongated body, and a closed state where a distal section of each of said plurality of extensions is located closer to said longitudinal axis compared to said tilted open state;

and wherein said distal section of each of said plurality of extensions is configured to be placed in contact with said LAA wall.

Example 45. A device according to example 44, wherein a distal section of an extension is bent in at least 90 degrees relative to a longitudinal axis of said extension.

Example 46. A device according to any one of examples 44 or 45, wherein a surface of said distal section contacting the LAA wall is smooth.

Example 47. A tissue grasper comprising:

an elongated tubular body having a proximal end and a distal end, wherein said proximal end is connected to a vacuum source;

a collapsible distal suction cup coupled to said distal end, defining a distal opening and an internal lumen, wherein said collapsible distal suction cup is configured to apply vacuum from said vacuum source through said distal opening on a LAA wall with a force sufficient to convex a portion of said LAA wall into said lumen, and to controllably collapse on said convexed portion of the LAA with a force sufficient to hold said convexed portion in said lumen.

Example 48. A tissue grasper according to example 47, wherein said collapsible distal cup comprises a plurality of spaced-apart extensions movably coupled to said elongated tubular body and arranged on a circumference of the elongated tubular body distal end, wherein in an open expanded state of said collapsible distal cup said plurality of spaced-apart extensions are tilted outwardly, and wherein in a collapsed state of said collapsible distal cup, said plurality of spaced-apart extensions move inwardly and press against said convexed portion of said LAA with a force sufficient to hold said convexed LAA portion in said lumen.

Example 49. A tissue grasper according to example 48, wherein each of said plurality of spaced-apart extensions has a proximal end movably coupled to said elongated tubular body and a distal end configured to be placed in contact with a wall of said LAA, wherein said distal end is bended in an angle larger than 90 degrees.

Example 50. A tissue grasper according to any one of examples 48 or 49, wherein at least some of said plurality of spaced-apart extensions are interconnected by at least one wire, wherein application of force on said wire controllably move said collapsible distal cup between said open expanded state and said collapsed state, by moving said at least some of said plurality of spaced-apart extensions.

Example 51. A tissue grasper according to any one of examples 48 to 50, comprises one or more layers of sheet material interconnecting said plurality of spaced-apart extensions to form an enclosed lumen of said collapsible distal cup.

Example 52. A tissue grasper according to example 51, wherein said one or more layers of sheet material comprise an elastic sheet material.

Example 53. A tissue grasper according to any one of examples 51 or 52, wherein in said collapsed state, portions of said one or more layers of said sheet material positioned between said plurality of spaced-apart extensions are configured to fold.

Example 54. A tissue grasper according to any one of examples 26 to 53, wherein at least a distal section of said elongated tubular body is controllably bendable.

Example 55. A tissue grasper according to any one of examples 47 to 44, wherein said collapsible distal suction cup comprises a distal leading edge configured to contact said LAA wall, and wherein said distal leading edge is covered with a smooth foldable fabric material configured to form a tight interface between said distal edge and said LAA wall.

Example 56. A tissue grasper according to example 55, wherein said collapsible distal suction cup comprises a plurality of ring holders coupled to a wall of said suction cup, and wherein each of said plurality of ring holders is configured to hold a wire shaped as a ring surrounding said collapsible suction cup, wherein application of force on said wire controllably moves said collapsible distal cup between an open expanded state and a collapsed state.

Example 57. A tissue grasper according to example 56, wherein said plurality of ring holders are coupled to an external surface or an internal surface of said suction cup wall.

Example 58. A system for LAA closure comprising:
a catheter having a distal opening introducible into the LA;
an LAA invaginator, comprising:
an elongated tubular body having a distal end with a distal opening and a proximal opening, wherein said elongated tubular body is shaped and sized to move within said catheter, to extend at least partly from the catheter distal opening into the LAA, and to contact a wall of said LAA with said elongated tubular body distal opening, wherein said elongated tubular body is configured to apply force on said LAA wall which is sufficient to convex a portion of said LAA wall into said elongated tubular body through said elongated tubular body distal opening;
at least one tissue grasper associated with said elongated tubular body, wherein said at least one tissue grasper is configured to move within said catheter and to grasp said convex portion of the LAA wall positioned within the elongated body;
wherein retraction of said at least one tissue grasper towards said catheter while grasping said convexed LAA portion, invaginates said LAA at least partly into said LA;
at least one ligator configured to pass within said catheter, to extend from said catheter distal opening, and to close said invaginated LAA.

Example 59. A system according to example 58 wherein said elongated tubular body distal end is configured to contact said LAA wall and is soft and/or flexible.

Example 60. A system according to any one of examples 48 or 59, wherein said at least one tissue grasper is configured to move over said elongated tubular body and said elongated tubular body distal end.

Example 61. A system according to any one of examples 58 to 60, wherein said at least one tissue grasper comprises a loop, and wherein said loop is configured to move between a closed state in which said loop is tightened, and an expanded state.

Example 62. A system according to example 61, wherein said at least one tissue grasper comprises a rod coupled to said loop, wherein said rod is configured to move said loop over said elongated tubular body and said elongated tubular body distal end.

Example 63. A system according to any one of examples 58 to 62, wherein said elongated tubular body terminates with an expanded portion at said distal end surrounding said distal opening of said elongated tubular body, wherein said expanded portion is configured to be placed in contact with said LAA wall.

Example 64. A system according to example 63, wherein said expanded portion configured to be placed in contact with the LAA wall is soft and/or flexible.

Example 65. A system according to any one of examples 58 to 64, wherein said at least one ligator comprises a clip configured to be closed around said invaginated LAA.

Example 66. A system according to any one of examples 58 to 64, wherein said at least one ligator comprises a loop configured to be tightened around said invaginated LAA.

Example 67. A system according to example 66, wherein said loop comprises a suture loop, a lasso or an elastic band.

Example 68. A system according to any one of examples 58 to 67, wherein said at least one ligator is configured to be irreversibly closed or tightened around said invaginated LAA.

Example 69. A system according to any one of examples 58 to 68, wherein said at least one ligator is configured to move over said at least one tissue grasper.

Example 70. A system according to any one of examples 58 to 68, comprising a LAA isolator configured to cover a LAA opening within the LA, to prevent flow of particles, debris and/or blood clots from said LAA into said LA.

Example 71. A system according to example 70, wherein said LAA isolator comprises a channel terminating with an expandable cover, wherein said expandable cover is configured to be in a collapsed state within said catheter and to expand within said LAA when extending out from the catheter.

Example 72. A system according to example 71, wherein said expandable cover comprises a plurality of pores which are shaped and sized to allow flow of blood between said LAA and said LA.

Example 73. A system according to any one of examples 71 or 72, wherein said at least one ligator is coupled to an inner surface of said expandable cover and is configured to detach from said expandable cover when closing said invaginated LAA.

Example 74. A tissue grasper comprising:

an elongated tubular body having a proximal end and a distal end, wherein said proximal end is connected to a vacuum source;

a suction cup coupled to said distal end, wherein said suction cup comprises a wall defining an inner lumen having a distal opening and a leading edge surrounding said distal opening; a plurality of extendable ring holders coupled to said suction cup wall surrounding said distal opening;

a tissue capturing ring associated with said plurality of extendable ring holders, wherein said suction cup is configured to apply vacuum from said vacuum source through said distal opening on a LAA wall contacting the leading edge with a force sufficient to convex a portion of said LAA wall into said lumen, and wherein said tissue capturing ring is configured to be advanced distally to said leading edge and to be controllably tightened around a base of said LAA wall portion located in said lumen.

Example 75. A tissue grasper according to example 74, wherein said plurality of extendable ring holders are configured to move between a folded state to an unfolded state in which said tissue capturing ring is advanced distally to said leading edge.

Example 76. A tissue grasper according to any one of examples 74 or 75, wherein said leading edge is covered with a smooth fabric material configured to form a tight interface between said distal edge and said LAA wall, and wherein said plurality of extendable ring holders are coupled to said smooth fabric material.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and figures makes apparent to those skilled in the art how embodiments of the invention may be practiced.

In the drawings:

FIGS. 2A-2J are schematic illustrations showing inversion, for example inwardly collapsing of a body lumen wall, according to some exemplary embodiments of the invention;

FIGS. 2K-2N are schematic illustrations showing grasping of a convexed, for example an inverted, body lumen wall, according to some exemplary embodiments of the invention;

FIGS. 5A-5I are schematic illustrations of a process for closure of the LAA, according to some exemplary embodiments;

FIGS. 8A-8I and FIGS. 9A-9C, are schematic illustrations and images showing closure of the LAA using a LAA closure system, according to some exemplary embodiments of the invention;

FIGS. 10A-10E are schematic illustrations of a retrieval device, according to some exemplary embodiments of the invention;

FIGS. 11A-11D are schematic illustrations showing different distal ends of a suction channel, according to some exemplary embodiments of the invention;

FIG. 12 is a schematic illustration of a steerable catheter, according to some exemplary embodiments of the invention;

FIGS. 14A-14C are schematic illustrations showing a tissue grasper having a plurality of clamps, according to some exemplary embodiments of the invention;

Figures 17A, 17B:
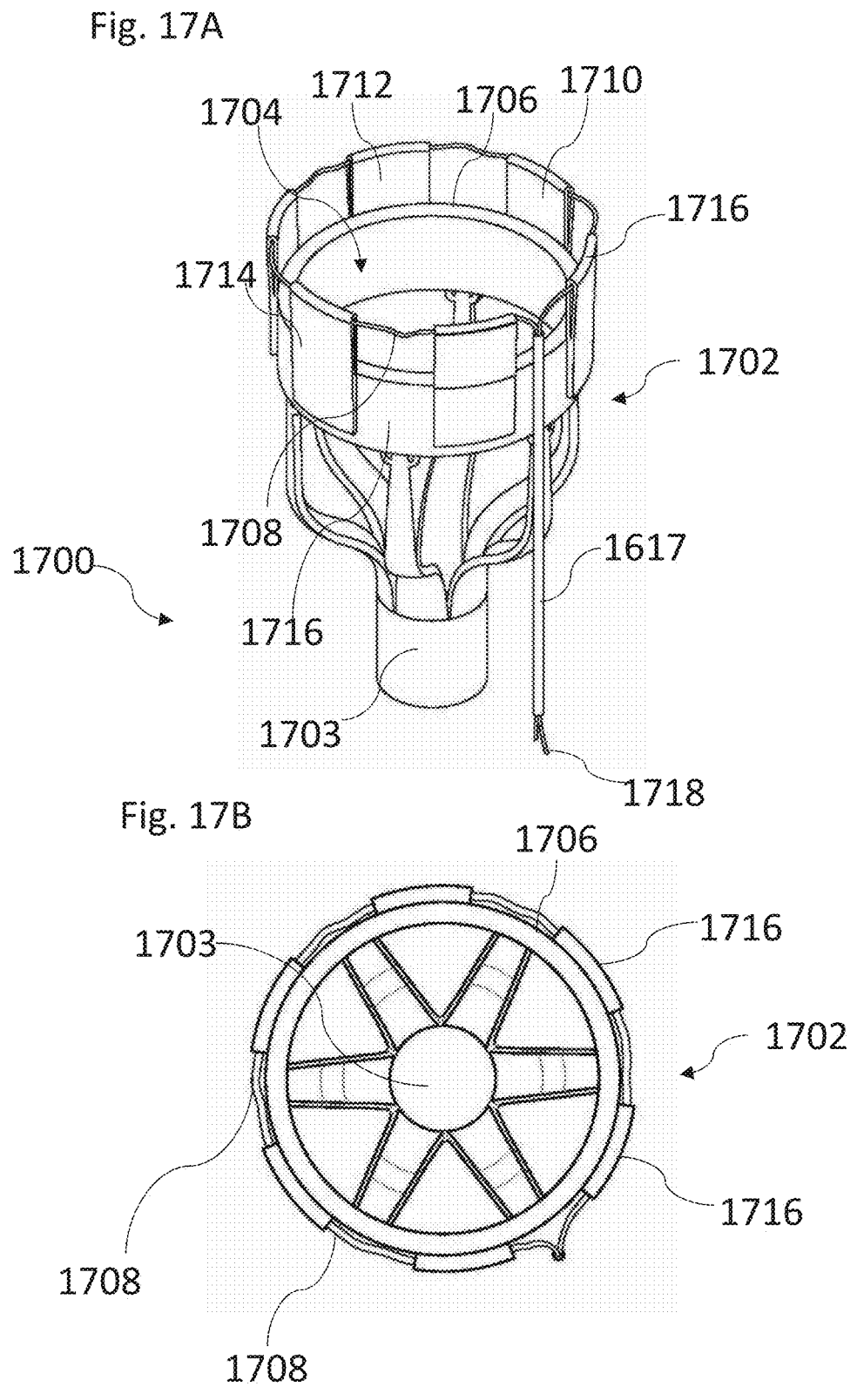

FIGS. 17A and 17B are schematic illustrations of a tissue grasper cup, for example a tissue grasper expandable cup, comprising a plurality of extendable ring holders configured to hold an extendable ring, according to some exemplary embodiments of the invention; and FIGS. 17C-17E are schematic illustrations showing grasping of a LAA wall portion using a tissue grasper expandable cup having an extendable ring, according to some exemplary embodiments of the invention.

DESCRIPTION OF SPECIFIC EMBODIMENTS OF THE INVENTION

Figure 1A:
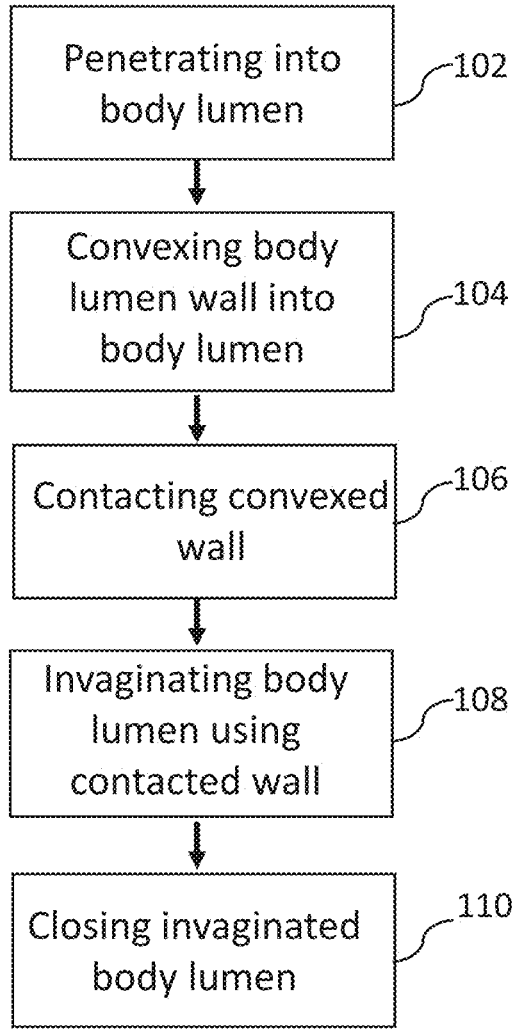
FIG. 1A is a flow chart of a general process for closure of a body lumen, according to some exemplary embodiments of the invention.

The present invention, in some embodiments thereof, relates to inversion of a body lumen wall, more particularly, but not exclusively, to inversion of a LAA wall.

Overview

An aspect of some embodiments relates to convexing, for example inverting, a portion of the LAA wall into the LAA. In some embodiments, the convexed portion, for example an inverted portion, of the LAA is grasped and used for invaginating the LAA. In some embodiments, a concaved portion of the LAA wall is convexed. In some embodiments, the LAA wall portion is convexed by applying force on an inner surface of the LAA wall from within the LAA. Alternatively, the LAA portion is convexed by penetrating at least partly into the LAA wall.

According to some exemplary embodiments, convexing of a portion of a LAA wall into the LAA, and grasping of the convexted portion are separated in time, for example the grasping is performed once the convexing is completed. Optionally, the convexing and the grasping are performed by two different elements, for example the convexing is performed by applying suction on a region of wall of the LAA, while the grasping is performed by pressing a small portion of the LAA wall region. Optionally, the pressed small portion has an area smaller in at least 30%, for example in at least 40%, in at least 50%, in at least 70% from an area of the LAA wall region onto which the suction is applied.

According to some embodiments, an inverted portion of a left atrial appendage (LAA) inside the LAA lumen is grasped. In some embodiments, the LAA is invaginated at least partly into the left atria (LA) using the grasped convexed LAA wall portion. In some embodiments, the LAA is invaginated completely into the LA using the grasped convexed portion.

According to some embodiments, at least one grasper is placed in contact with the inverted portion of the LAA wall within the LAA lumen. Optionally, the at least one grasper is placed around the inverted portion of the LAA wall. Additionally, the at least one grasper is retracted into the LA while attached to the grasped convexed portion, for example to allow the at least partial invagination of the LAA into the LA. In some embodiments, following invagination of the LAA into the LA, the at least one grasper is detached from the LAA wall.

According to some embodiments, a portion of the LAA wall is partly inverted into the LAA lumen, for example by applying vacuum of the LAA wall. In some embodiments, a level of vacuum applied on the LAA wall is high enough to invert the LAA wall portion into the LAA lumen, but is too low for invaginating the LAA at least partly into the LA. In some embodiments, the level of the vacuum applied on the LAA wall is in a range of 50 mmHG-760 mmHG, for example 50 mmHG-100 mmHG, 50 mmHG-200 mmHG, 100 mmHG-300 mmHG, 200 mmHG-500 mmHG, 400 mmHG-760 mmHG or any intermediate, smaller or larger range of pressure levels.

According to some exemplary embodiments, the LAA wall is partially inverted into the LAA lumen by changes in pressure levels within the LA, for example during beating of the heart. Alternatively or additionally, the LAA wall is partially inverted by a force applied on the outer surface of the LAA from outside the heart. Alternatively, the LAA wall is partially inverted into the LAA lumen, by pinching and retracting an inner surface of the LAA wall.

According to some embodiments, the invaginated LAA is closed by at least one ligator, for example a loop, a suture loop, a snare, a mesh, that is fastened, for example tightened around the invaginated LAA. Optionally, the at least one ligator is fastened around a base of the invaginated LAA. Optionally, the at least one ligator is irreversibly fastened around the invaginated LAA. In some embodiments, the LAA is closed by the at least one grasper, irreversibly coupled to the LAA wall, and the at least one ligator. Alternatively, the invaginated LAA is closed only by the at least one ligator.

A potential advantage of using different tools and/or applying different forces for convexing and grasping may be to allow application of relative weak forces on the LAA wall during an invagination process of the LAA into the LA. For example, in order to invaginate the LAA into the LA using only vacuum suction, a relative strong suction force is required for both convexing, and grasping the convexed LAA portion during invagination, by using a large suction cup within the LAA. However, when using vacuum suction only for the convexing of the LAA wall, or by applying an additional type of force only during invagination, a much weaker vacuum force is needed for the convexing and a much smaller suction cup is introduced into the LAA. Application of weaker forces on the LAA wall, and using smaller tools within the LAA during invagination may reduce a risk of damaging the LAA tissue, thereby increasing safety of a LAA invagination procedure.

An aspect of some embodiments relates to a tissue grasper that comprises a vacuum application portion configured to apply vacuum on a wall of a tissue, for example on a wall of the LAA, and a mechanical tissue capturing portion. In some embodiments, the mechanical tissue capturing portion comprises a wire shaped as a ring configured to collapse a suction cup of the vacuum application portion on tissue located inside the suction cup. Alternatively or additionally, the tissue capturing portion of the tissue grasper is configured to tighten the ring around a base of a tissue located within the suction cup.

According to some embodiments, the tissue capturing portion is coupled to the vacuum application portion or is associated with the vacuum application portion. In some embodiments, the ring position is fixed relative to a position of a leading edge of the suction cup. Alternatively, the ring is configured to be advanced distally to the leading edge of the cup, for example to allow grasping of a larger portion of the tissue, for example the LAA wall. In some embodiments, the ring is configured to be advanced or to be retracted relative to the suction cup leading edge, by manipulating at leats one wire and/or at least one shaft coupled to the ring. In some embodiments, the shaft is flexible. Alternatively the shaft is rigid in an axial direction.

According to some exemplary embodiments, the ring is coupled to the suction cup by a plurality of ring holders coupled to the suction cup wall. In some embodiments, the plurality of ring holders are spaced-apart on the wall of the suction cup. In some embodiments, the plurality of ring holders surrounds the suction cup, for example surround the distal opening of the suction cup. In some embodiments, the plurality of ring holders are coupled to an internal surface or an external surface of the suction cup wall.

According to some exemplary embodiments, the ring holders are flexible, extendable or stretchable, for example to allow relative movement of the ring coupled to the ring holders relative to the leading edge of the suction cup. Optionally, the ring holders are at least partly formed from at least one layer of a fabric, for example a foldable fabric. Optionally, the ring holders are shaped as patches. In some embodiments, the ring holders are coupled to at least one layer of material, for example at least one layer of fabric covering the suction cup and/or the leading edge of the suction cup.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Body Lumen Closure

According to some exemplary embodiments, a body lumen, for example the LAA is closed, for example to prevent entry and/or accumulation of unwanted particles into the body lumen. Alternatively, or additionally, the body lumen is closed, for example to prevent rupture of the body lumen walls. In some embodiments, the body lumen is closed by inwardly invagination of the body lumen and irreversibly fastening of the invaginated body lumen. Reference is now made to FIG. 1A, depicting a process for invagination and closure of a body lumen, according to some exemplary embodiments of the invention.

According to some exemplary embodiments, a body lumen closure device is introduced into the body lumen at block 102. In some embodiments, the device is introduced into the body lumen through at least one natural body opening. Alternatively, the device is introduced into the body lumen through at least one artificial body opening formed by a surgical process.

According to some exemplary embodiments, a portion of a wall of the body lumen, for example an outwardly curved wall portion, or a concaved wall portion is convexed, for example inverted, at block 104. In some embodiments, the wall portion is inverted inwardly, into the body lumen. In some embodiments, the wall portion is inverted into the body lumen to a distance that is sufficient in order to hold the inverted body lumen wall. In some embodiments, the wall portion is inverted into the body lumen to a distance that is sufficient in order to grasp the inverted wall with at least one tissue grasper, for example a clip, a lasso, a loop, and/or a suture loop. In some embodiments, the wall is inverted to a distance of up to 2 cm, for example up to 1 cm, up to 0.7 cm, up to 0.5 cm, up to 0.3 cm or any intermediate, smaller or larger distance from portions of the body lumen wall that were not inverted. In some embodiments, the portion of the body lumen wall is inverted into the body lumen to a distance of up to 50%, for example up to 30%, up to 20%, up to 5% or any intermediate, smaller or larger percentage value from a distance between the body lumen wall and an opening of the body lumen.

According to some exemplary embodiments, the portion of the body lumen wall is inverted by a force applied on the wall from within the body lumen, for example by the body lumen closure device. Alternatively, the wall is inverted by a force applied on the wall from outside the body lumen.

According to some exemplary embodiments, the convexed body lumen wall is contacted at block 106. Additionally, the at least one grasper is attached to the inverted wall portion, at block 106. In some embodiments, the convexed body lumen wall is held in a convexed state at block 106. In some embodiments, at least one grasper contacts the convexed body lumen wall, for example is attached around the inverted wall portion. In some embodiments, the at least one grasper is optionally irreversibly attached to the inverted wall portion. Alternatively, the at least one grasper is optionally reversibly attached to the inverted wall portion. In some embodiments, the at least one grasper comprises a loop, a lasso, a suture loop, a snare, a clip and/or a wire mesh. In some embodiments, the at least one grasper is coupled to the device introduced into the body lumen at block 102.

According to some exemplary embodiments, the body lumen is at least partly invaginated using the convexed wall portion, at block 108. In some embodiments, the body lumen is at least partly invaginated using the convexed wall portion through the body lumen opening. Optionally, the body lumen is invaginated by retracting the at least one grasper, while the at least one grasper is attached to the inverted wall portion. In some embodiments, the at least one grasper is retracted using the body closure lumen device. Optionally, the inverted wall portion is twisted in a timed relationship with the invagination, for example before, during and/or after the invagination. Optionally, the inverted wall portion is twisted using the at least one grasper, for example by twisting or rotating the at least one grasper.

According to some exemplary embodiments, the invaginated body lumen is closed at block 110. In some embodiments, the invaginated body lumen is closed by optionally contacting, for example attaching at least one ligator to the invaginated body lumen. In some embodiments, the at least one ligator is optionally positioned around the invaginated body lumen, for example around a base of the invaginated body lumen. Optionally, the at least one ligator is irreversibly tightened around the invaginated body lumen. In some embodiments, the at least one ligator comprises a loop, a lasso, a suture loop, a snare, a band, a clip and/or a wire mesh. In some embodiments, the at least one ligator is tightened around the invaginated body lumen, for example around a base of the invaginated body lumen, to reduce a volume of the invaginated body lumen.

According to some exemplary embodiments, the at least one grasper is released from the invaginated body lumen, after the attachment of the at least one ligator. Alternatively, the at least one grasper is disconnected from the body lumen closure device while remaining attached to the invaginated body lumen.

According to some exemplary embodiments, the body lumen closure device is detached from the at least one ligator following closure of the invaginated body lumen at block 110. Addition, the body closure device is removed from the body following the detachment.

Exemplary LAA Closure

Figure 1B:
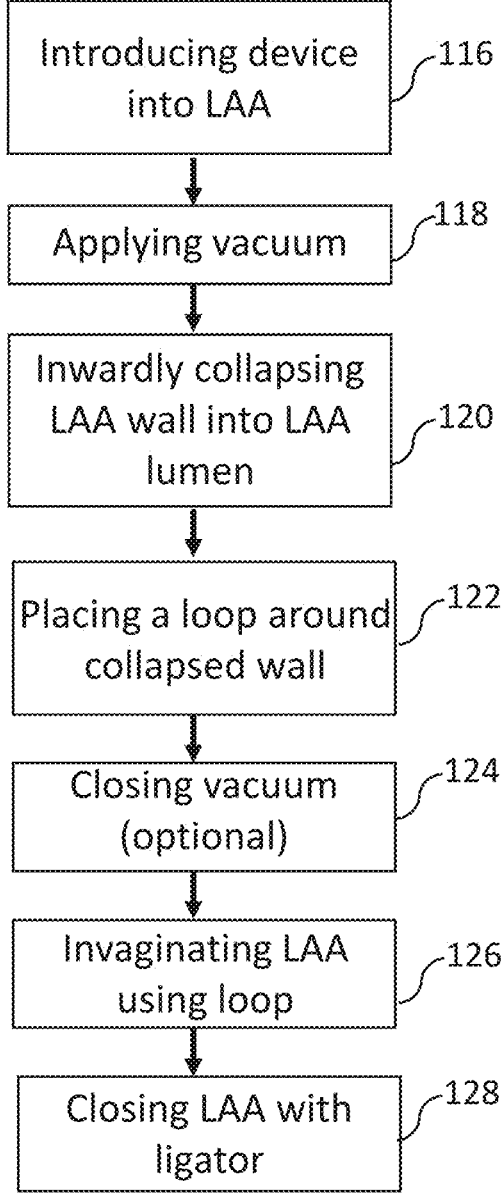
FIG. 1B is a flow chart of a process for closure of the LAA, according to some exemplary embodiments of the invention.

According to some exemplary embodiments, the LAA is closed, for example to prevent formation, accumulation and/or release of blood clots from the LAA lumen into the blood stream. Reference is now made to FIG. 1B, depicting a general process for closure of the LAA, according to some exemplary embodiments of the invention.

According to some exemplary embodiments, a LAA closure device is introduced into the LAA lumen at block 116. In some embodiments, an LAA invaginator of the LAA closure device is introduced into the LAA lumen. Optionally, a distal end of a suction tube of the LAA closure device is introduced into the LAA lumen. In some embodiments, the LAA closure device is introduced into the LAA lumen via the LA, for example through an LAA opening in the LA. In some embodiments, a working channel of the LAA closure device is transeptally introduced into the LA, for example from the right atrium.

According to some exemplary embodiments, vacuum is applied by the LAA closure device at block 118. In some embodiments, the vacuum is applied from at least one distal opening of a suction tube of the LAA closure device, positioned within the LAA lumen. In some embodiments, the suction tube, for example the at least one distal opening of the suction tube is placed in contact with the LAA wall during the vacuum application.

According to some exemplary embodiments, a portion of the LAA wall is inverted, for example inwardly collapsed into the LAA lumen, at block 120. In some embodiments, the portion of the LAA is inverted by the applied vacuum. In some embodiments, the inverted LAA wall portion is a portion of the LAA wall placed in contact with the at least one distal opening of the suction tube. In some embodiments, the LAA wall portion is inverted into the suction tube, for example via the at least one distal opening of the suction tube. Optionally, the LAA wall is inverted up to 1 cm, for example up to 0.7 cm, up to 0.5 cm, up to 0.3 cm or any intermediate, shorter or longer length, from the LAA wall into the LAA lumen.

According to some exemplary embodiments, at least one grasper, for example a loop is placed around the inverted portion of the LAA wall at block 122. In some embodiments, the loop comprises a suture loop, a lasso or a snare. In some embodiments, the loop is placed and tightened around the inverted LAA wall while vacuum is applied, for example to hold the inverted LAA wall during loop placement and/or tightening. In some embodiments, the loop is placed and/or tightened around the inverted portion of the LAA wall in an atraumatic way, for example without penetrating through the LAA wall and/or without causing damage to the LAA wall. In some embodiments, the at least one loop is coupled to the suction tube and/or to the LAA closure device.

According to some exemplary embodiments, vacuum is optionally closed at block 124. In some embodiments, once the at least one loop is placed around the inverted portion of the LAA wall, vacuum application is optionally stopped. In some embodiments, vacuum application is stopped after tightening of the loop, for example to prevent return of the inverted LAA wall portion into an outwardly curved shape, for example, a convexed shape, when vacuum application stops.

According to some exemplary embodiments, the LAA is invaginated using the at least one loop, at block 126. In some embodiments, the LAA is at least partly or completely invaginated into the LA, for example through the LAA opening, using the loop. Optionally, the LAA is invaginated using the loop and vacuum application. In some embodiments, the LAA is invaginated at block 126 into a LAA reshaper located in the LA, for example over the LAA opening. Alternatively, the LAA is invaginated at block 126 into a LAA separator, separating the LAA lumen from the LA, for example to prevent flow of particles, debris, and/or blood clots from the LAA into the blood stream. Alternatively, or additionally, the LAA is invaginated into at least one LAA ligator configured to close the invaginated LAA.

According to some exemplary embodiments, at least one LAA ligator is attached to the invaginated LAA, at block 128. In some embodiments, the at least one LAA ligator is optionally tightened, for example irreversibly tightened around the invaginated LAA. In some embodiments, the at least one LAA ligator comprises a loop, a suture loop, a clip, a snare, and/or a lasso. In some embodiments, the at least one LAA ligator is attached to the invaginated LAA, inside the LA.

According to some exemplary embodiments, once the LAA ligator is tightened around the invaginated LAA, for example around a base of the invaginated LAA, the loop used for invagination is released from the LAA wall and retracted from the LA. Alternatively, the loop is disconnected from the LAA closure device and remains attached to the LAA wall. In some embodiments, following closure of the LAA, the LAA closure device is disconnected from the LAA ligator fixedly attached to the invaginated LAA, and retracted from the LA.

According to some exemplary embodiments, the LAA is closed by advancing the at least one loop used for invagination towards a base of the invaginated LAA. In some embodiments, once the at least one loop is located at a desired position on the invaginated LAA, the LAA closure is disconnected from the loop.

Exemplary Inversion of Body Lumen Wall

According to some exemplary embodiments, a portion of a body lumen wall, for example a portion of the LAA wall, is inverted into the body lumen, for example into the LAA. In some embodiments, the portion of the wall is inverted until reaching an inverted portion which is large enough to be held by at least one grasper. In some embodiments, the portion of the wall is inverted to a distance of up to 2 cm, for example up to 1 cm, up to 0.5 cm, up to 0.3 cm or any intermediate, smaller or larger distance from the LAA wall. Reference is now made to FIGS. 2A-2H, depicting inversion of a portion of the LAA, according to some exemplary embodiments of the invention.

According to some exemplary embodiments, for example as shown in FIG. 2A, a portion of wall 204 of body lumen 202, for example LAA, is inverted by application of force on the LAA wall 204 from outside the LAA 202. In some embodiments, the applied force 206 inverts an outwardly curved portion of the LAA wall, for example LAA wall portion 208, into the LAA 202, for example as shown in FIG. 2B. In some embodiments, the force is applied on an outer surface of the wall 204. In some embodiments, the force is applied by a device located outside the LAA. Alternatively, the force is applied by a device located within the LAA.

According to some exemplary embodiments, for example as shown in FIGS. 2C, a force is applied on the wall 204 from within the LAA, for example by a device located within the LAA. In some embodiments, a force 210 applied on the wall 204 from within the LAA 202, inverts an outwardly curved portion of the LAA wall, for example LAA wall portion 208, into the LAA 202, for example as shown in FIG. 2D.

According to some exemplary embodiments, for example as shown in FIGS. 2E and 2F, a force is applied on the outer surface of the wall 204 by a device 212 located within the LAA 202. In some embodiments, the device 212 penetrates through wall 204, and a tip 214 of the device is placed in contact with the outer surface of the wall 204. Optionally, the tip 214 is an expandable tip, for example to increase contact area with the outer surface of wall 204. In some embodiments, for example as shown in FIG. 2F, retraction of the device 212 into the LAA 202, inverts the wall portion 214 into the LAA 202.

According to some exemplary embodiments, for example as shown in FIGS. 2G and 2H, a device 216 located in the LAA 202, is partly inserted into wall 204, without penetrating the wall 204. In some embodiments, the device 216 is reversibly coupled to the wall 204. In some embodiments, retraction of the device into the body LAA 202, inverts wall portion 218 into the LAA 202.

According to some exemplary embodiments, for example as shown in FIGS. 2I and 2J, a portion of the LAA wall is inverted by application of vacuum from within the LAA 202. In some embodiments, for example as shown in FIG. 2I a suction tube 218 has a distal opening 220 that is placed in contact with the inner surface of the LAA wall 204. In some embodiments, application of vacuum through the distal opening 220 inverts wall portion 222 into the LAA 202, for example into an inner lumen 224 of the suction tube 218.
Exemplary Grasping of Inverted Wall According to some exemplary embodiments, at least one tissue grasper is attached to an inverted portion of the body lumen wall, for example an inverted portion of the LAA wall. In some embodiments, the at least one tissue grasper is used to invaginate the LAA at least partly into the LA. Reference is now made to FIGS. 2K-2N, depicting different types of tissue graspers, according to some exemplary embodiments of the invention.

According to some exemplary embodiments, the tissue grasper is reversibly attached to the inverted portion of the LAA wall, for example to allow release of the tissue grasper when closing the invaginated LAA. Alternatively, the tissue grasper is irreversibly attached to the inverted portion of the LA wall, for example when the tissue grasper is used for closing of the invaginated LAA.

According to some exemplary embodiments, for example as shown in FIG. 2K, the at least one tissue grasper, for example tissue grasper 224 comprises a distal anchor, for example anchor 226 configured to penetrate at least partly into the inverted LAA wall 222. In some embodiments, the at least one anchor comprises at least one pin, at least one rod, and/or at least one screw. In some embodiments, the at least one anchor penetrates through the inverted LAA wall. In some embodiments, the tissue grasper, for example the tissue grasper 224 is attached, for example reversibly attached, to the convexed LAA wall 222, while suction is applied on the convexed LAA wall by the suction tube 217. Optionally, the suction tube is retracted from the LAA after attaching the tissue grasper to the convexed LAA wall, for example to allow invagination of the LAA into the LA using only the tissue grasper. Alternatively, the suction tube applies vacuum on the convexed LAA wall while the tissue grasper is attached to the convexed LAA wall, for example to allow invagination of the LAA into the LA using both suction from the suction tube and grasping by the tissue grasper.

According to some exemplary embodiments, for example as shown in FIG. 2L, the at least one tissue grasper 228 comprises a pair of forceps 230, configured to hold the inverted LAA wall in at least two contact points, for example at least two contact points at opposite sides of the inverted wall 222. Optionally, the at least one tissue grasper 228 comprises a locking mechanism configured to lock the forceps 230 when the forceps hold the inverted LAA wall 222, and to unlock the forceps in order to release the forceps from the inverted LAA wall 222.

According to some exemplary embodiments, for example as shown in FIG. 2M, the at least one tissue grasper 232 comprises at least one loop 234, configured to be tightened around the inverted LAA wall 222. Optionally, the at least one grasper comprises a reversibly tightening mechanism, for tightening and loosening of the loop. In some embodiments, the at least one loop comprises a suture loop or a lasso. In some embodiments, following the tightening of the at least one loop around the inverted LAA wall, the at least one loop is used to invaginate the LAA at least partly into the LA, for example by retracting or pulling the at least one grasper into the LA.

Figure 3:
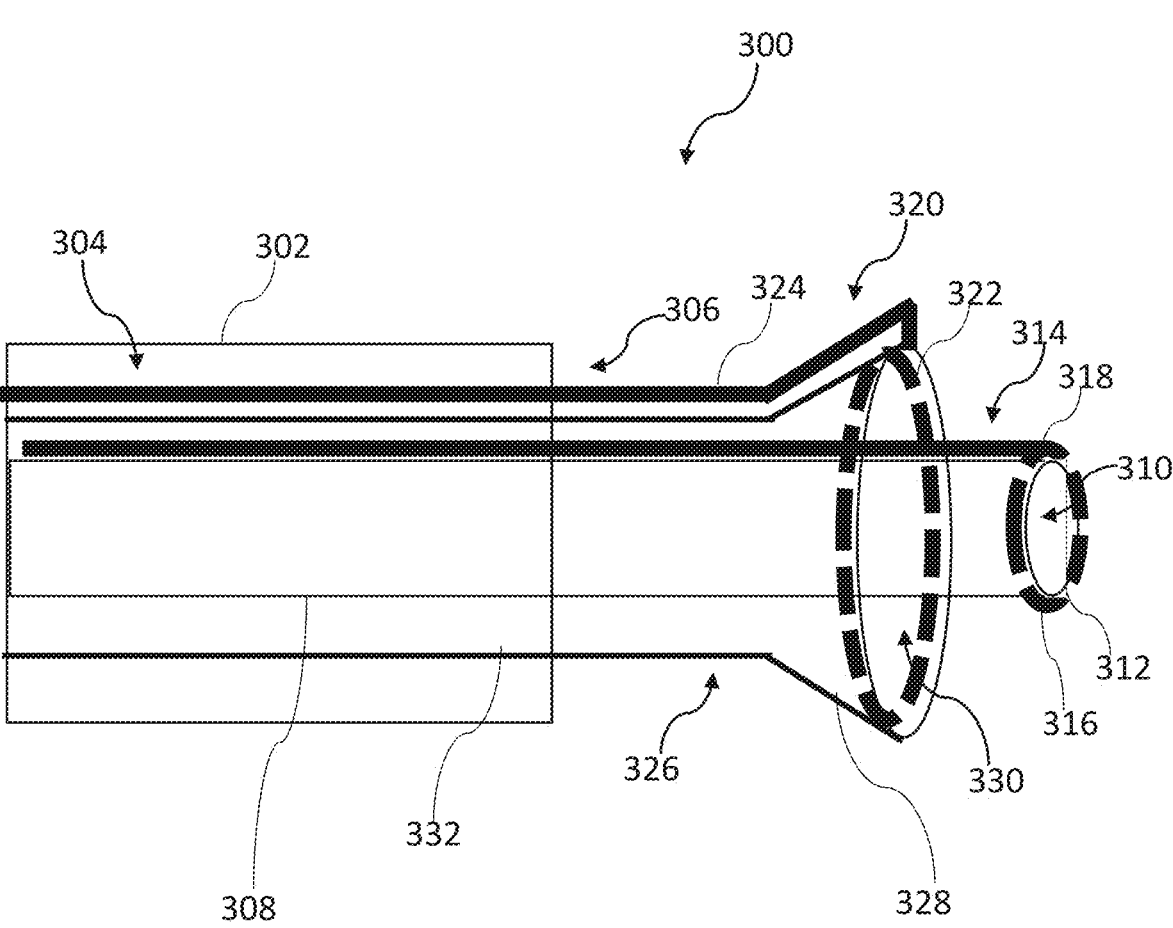
FIG. 3 is a schematic block diagram of a system or device for closure of the LAA, according to some embodiments of the invention.

According to some exemplary embodiments, for example as shown in FIG. 2N, the LAA is invaginated using the at least one loop 234, and while applying vacuum by suction tube 217 on the inverted LAA wall 222.
Exemplary LAA Manipulating Device Reference is now made to FIG. 3, depicting a device for manipulating the LAA, according to some exemplary embodiments of the invention.

According to some exemplary embodiments, a device 300 for manipulating the LAA comprises an elongated and hollow guide instrument, for example instrument 302, shaped and sized to be introduced into the LA. In some embodiments, the device 300 is a tube. In some embodiments, the instrument 302 is optionally shaped and sized to be transeptally introducible into the LA. Optionally, the instrument 302 is shaped and sized and/or flexible to be transvasculary introducible into the heart, for example into the right atrium (RA). In some embodiments, the maximal outer diameter of the instrument 302 is in a range of 5-7 French (Fr), for example 5-5.5 Fr, 5-6 Fr, 6-7Fr or any intermediate, smaller or larger value. In some embodiments, the maximal outer diameter of the instrument 302 is in a range of 1.5-3 mm, for example 1.5-2 mm, 1.5-2.5 mm, 2-2.5 mm, 2-3 mm or any intermediate, smaller or larger range of values. In some embodiments, the maximal outer diameter of device 300 is the maximal outer diameter of the instrument 302.

According to some exemplary embodiments, the instrument 302 defines an inner lumen, for example a working channel 304 having a distal opening 306.

According to some exemplary embodiments, the device 300 comprises at least one elongated suction tube, for example suction tube 308 having a distal opening 310. In some embodiments, the suction tube is shaped and sized to pass within said working channel 304, and to extend out, at least partly from the distal opening 306 of the suction channel. In some embodiments, a distal tip 312 of the suction tube 308, surrounding the distal opening 310, is shaped and sized to be introducible through a LAA opening in the LA, into the LAA.

According to some exemplary embodiments, the distal tip 312 is soft and/or flexible, for example to contact an inner surface of the LAA wall without causing damage to the LAA wall. In some embodiments, a proximal opening of the suction tube is connectable to a vacuum source. In some embodiments, application of vacuum within the suction tube 308 and through the distal opening 310, when the distal tip 312 contacts the LAA wall, inverts a portion of the LAA wall into the suction tube 308.

According to some exemplary embodiments, the suction tube 308 is bendable, for example controllably bendable. In some embodiments, at least a portion of the suction tube, for example a distal section of the suction tube is controllable steerable, for example controllably bendable, for example to allow steering and/or bending of a distal end of the suction tube when steering the suction tube distal end within the LAA. In some embodiments, a maximal width of the suction tube distal opening 310 is up to 1.5 mm, for example up to 1 mm, up to 0.7 mm, up to 0.5 mm or any intermediate, smaller or larger value. In some embodiments, a width of the suction tube distal opening 310 is in a range of about 0.5 mm to about 12 mm, for example about 0.5 mm to about 3 mm, about 1 mm to about 4 mm, about 2 mm to about 5 mm, about 4 mm to about 8 mm, about 5 mm to about 10 mm, about 6 mm to about 12 mm or any intermediate, smaller or larger range of values.

According to some exemplary embodiments, the distal tip 312 is an expandable distal tip, configured to travel within the working channel 304 in a collapsed state, and to expand in the LA or in the LAA, for example after exiting through a distal opening 306 of the working channel 304. In some embodiments, the distal tip 312 expands into a concave shape, for example to allow vacuum application of a larger area of the LAA wall.

According to some exemplary embodiments, the device 300 comprises at least one tissue grasper, for example grasper 314. In some embodiments, the at least one grasper is shaped and sized to move within the working channel 304. In some embodiments, the grasper 314 is shaped and sized to slide over the suction tube 308 and the distal tip 312. Alternatively, the at least one tissue grasper is shaped and sized to move within the suction tube 308 and to optionally extend out at least partly from said suction tube distal opening 310. In some embodiments, the at least one tissue grasper 314 is coupled to the suction tube 308.

According to some exemplary embodiments, the at least one tissue grasper 314 comprises a loop 316, for example a ring, configured to pass over the suction tube 308, for example when the loop 316 is in a relaxed state. In some embodiments, the at least one tissue grasper 314 comprises a shaft 318, for example a flexible and/or a bendable shaft. In some embodiments, the shaft 318 is connected, for example mechanically connected, to the loop 316. In some embodiments, rotation, twisting and/or maneuvering of the shaft 318, tightens and/or loosens the loop 316. Optionally, maneuvering of the shaft 318, locks the loop 316 at a tightened state and/or at a loose state. Optionally, maneuvering of the shaft 318 allows, for example, to disconnect the shaft 318 from the loop 316, for example when the loop is at a tightened state. Alternatively, the shaft 318 is hollow, and a wire connected to the loop 316 travels within the inner lumen of the shaft 318.

According to some exemplary embodiments, the loop 316 comprises a suture loop, a wire, a lasso, and/or a wire mesh. In some embodiments, the loop 316 and the shaft 318 are shaped and sized to move, within the working channel 304 and over the suction tube 308 and the suction tube. In some embodiments, the loop 316, for example in a loose and/or open state, is shaped and sized to move over the suction channel distal tip 312.

According to some exemplary embodiments, the device 300 comprises at least one ligator, for example ligator 320 shaped and sized to move within the working channel 304, and over the at least one tissue grasper 314. Alternatively, or additionally, the at least one ligator 320 is shaped and sized to pass over the suction tube 308. In some embodiments, the at least one ligator 320 is configured to move between a loose or open state to a tightened state, for example an irreversibly tightened state. In some embodiments, the at least one ligator 320 comprises a loop, for example loop 322. In some embodiments, the loop 322 comprises a suture loop, a band, a wire, a lasso, and/or a wire mesh.

According to some exemplary embodiments, the at least one ligator 320 comprises a shaft 324, for example a flexible and/or a bendable shaft mechanically connected to the loop 322. In some embodiments, maneuvering of the shaft 324 tightens, for example irreversibly tightens the loop 322 around tissue located within the loop 322, for example LAA tissue. In some embodiments, the shaft 324 is configured to controllably tighten the loop 322 around the tissue with a force that does not cause damage, for example tearing, rupture and/or perforation of the tissue. In some embodiments, the shaft 324 is optionally connectable to a control unit, for example a control handle, located outside the body.

According to some exemplary embodiments, the device 300 comprises at least one elongated hollow LAA isolator 326 terminating with a distal cover 328, for example an expandable distal cover. In some embodiments, the distal cover 328 is shaped as a concave distal cover. In some embodiments, the distal cover 328 is configured to expand from the working channel 304 in the LA, and to be positioned in contact with tissue of the LA wall surrounding a LAA opening within the LA. In some embodiments, the expandable distal cover 328 surrounds a distal opening 330 of a channel 332 of the hollow LAA isolator 326. In some embodiments, the channel 332, for example a suction channel, terminates with the distal cover 328. In some embodiments, a proximal opening of the LAA isolator channel 332 is connectable to a vacuum source.

According to some exemplary embodiments, the expandable distal cover 328 is configured to contact the LA wall around the LAA opening, and to form a sealed flow path between the LAA lumen and the channel 332. In some embodiments, forming the sealed flow path allows to prevent entry of particles, for example blood clots, tissue particles and/or debris from the LAA lumen into the LA, optionally when the LAA is manipulated. In some embodiments, application of vacuum through the LAA isolator channel 332 allows, for example to actively remove the particles from the LAA before, during and/or after manipulation of the LAA.

According to some exemplary embodiments, the expandable distal cover 328 is comprises a wire mesh, covered with a sheet of material. In some embodiments, the wire mesh is optionally formed from a shape-memory alloy, for example Nitinol. In some embodiments, the expandable distal cover expands in a relaxed state, and/or is collapsed when retracted or positioned within the working channel 304. In some embodiments, when expanded, a width of the distal cover 328 is larger than a maximal width of the opening 306. In some embodiments, when expanded the distal cover 328 has a maximal width in a range of about 1 mm to about 30 mm, for example about 1.5 mm to about 5 mm, about 2 mm to about 6 mm, about 5 mm to about 10 mm, about 2 mm to about 10 mm, about 6 mm to about 15 mm or any intermediate, smaller o larger range of values.

According to some exemplary embodiments, the at least one ligator 320 is coupled at least partly to the LAA isolator 326. In some embodiments, the loop 322 of the at least one ligator 320 is coupled to the expandable distal cover 328, for example close to the distal opening 320. In some embodiments, the loop 322 is coupled to the inner surface of the distal cover 328. Alternatively, the loop 322 is coupled to the outer surface of the distal cover 328. In some embodiments, the shaft 324 connected to the loop 322 passes within the channel 332. In some embodiments, the shaft 324 is coupled at least partly to the inner surface of the channel 332. Alternatively, the shaft 324 passes outside the channel 332, and is optionally coupled to the outer surface of the channel 332. In some embodiments, the at least one ligator 320 and the at least one LAA isolator 326 are at least partly coupled to each other when moving within the working channel 304, for example into the LA.

According to some exemplary embodiments, the loop 322 is coupled, for example reversibly attached to an inner surface of the distal cover 328, at a distance of up to 5 cm, for example up to 3 cm, up to 1 cm, up to 0.5 or any intermediate, smaller or larger value from the opening 330. In some embodiments, movement of the shaft 324, for example pushing, pulling, retracting and/or turning detaches the loop 322 from the cover 328. Additionally, or optionally, movement of the shaft 324 tightens the loop 322 around tissue located within the distal cover 328. Additionally, or optionally, movement of the shaft 324 disconnects the shaft 324 from the loop 322, for example when the loop is tightened around a tissue.

According to some exemplary embodiments, the LAA isolator 326 is a LAA reshaper, configured to reshape a portion of the LAA invaginated into the distal cover, for example before tightening of the at least one ligator to the invaginated LAA. In some embodiments, reshaping of the invaginated LAA allows, for example to reduce the volume and/or the size of the invaginated LAA tissue left inside the LA after LAA closure by the at least one ligator.

According to some exemplary embodiments, a LAA manipulating device comprises the guiding instrument 302 having the working channel 304, the suction tube 308, the at least one tissue grasper 314, the at least one ligator 320, and optionally the LAA isolator. Alternatively, for example in embodiments when a partial inversion of the LAA into the tissue grasper is based on changes of pressure in the heart or on application of force from outside the heart, the LAA manipulating device comprises the guiding instrument 302 having the working channel 304, the at least one tissue grasper 314, the at least one ligator 320, and optionally the LAA isolator 326.

Exemplary Detailed LAA Closure Procedure

Figure 4:
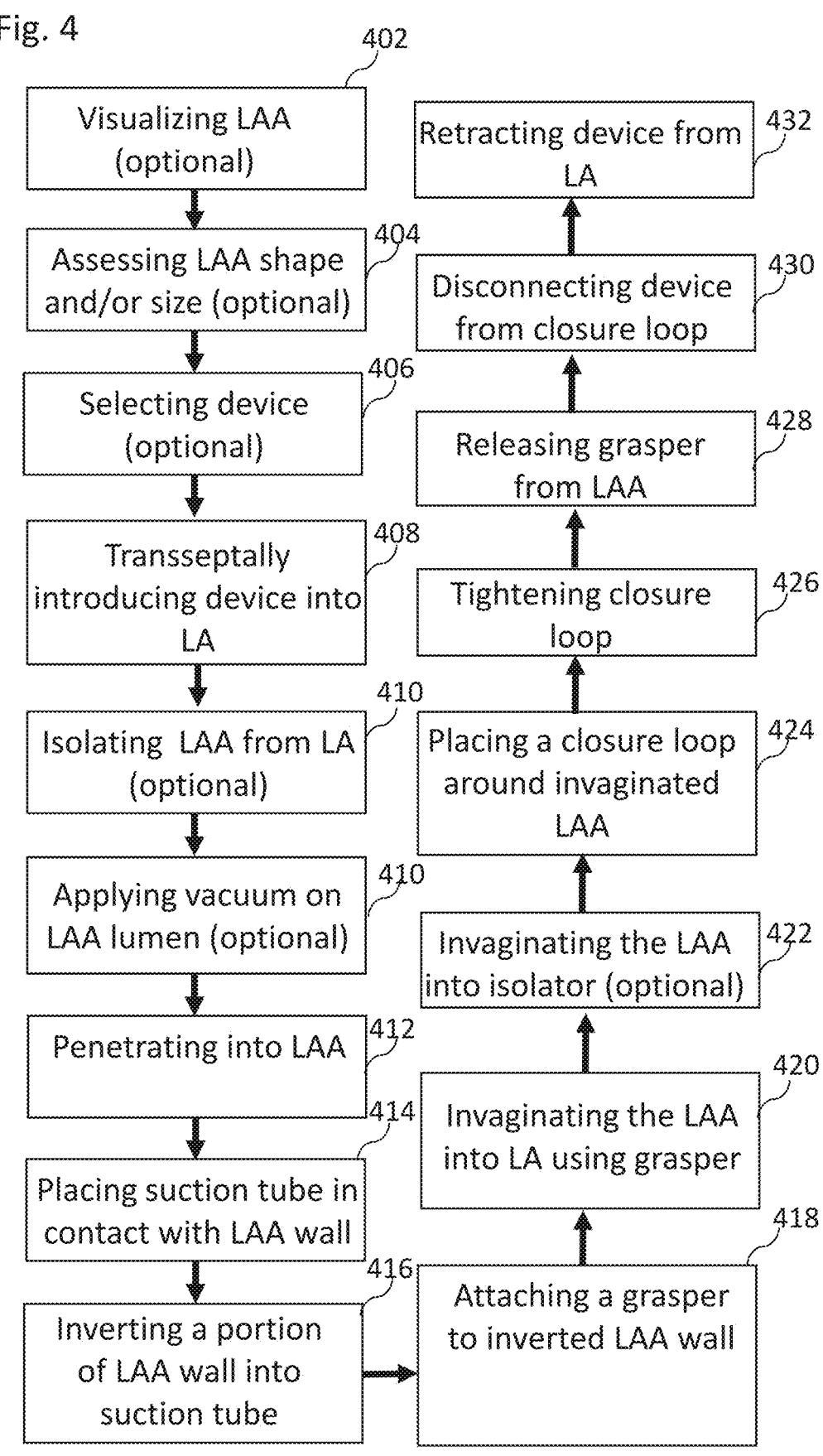
FIG. 4 is a flow chart of a detailed process for closure of the LAA, according to some exemplary embodiments of the invention.

Reference is now made to FIG. 4, depicting a detailed process for closure of the LAA, according to some exemplary embodiments of the invention.

According to some exemplary embodiments, the LAA of a subject is optionally visualized, at block 402. Optionally, the LAA opening in the LA is visualized at block 402. In some embodiments, the LAA is visualized from within the body, for example using a catheter, an endoscope or an imaging device. Alternatively, the LAA is visualized from outside the body, for example using at least one imaging device, for example x-ray, ultrasound, computed tomography (CT), or Magnetic resonance imaging (MRI).

According to some exemplary embodiments, a LAA shape and/or size is assessed at block 404. In some embodiments, the LAA shape and/or size is assessed, based on the visualization results. In some embodiments, a width and/or shape of the LAA opening in the LA is assessed at block 404, for example based on the visualization results. In some embodiments, a depth, and/or a distance of a LAA wall region from the LAA opening is assessed.

According to some exemplary embodiments, a LAA closure device, for example a LAA manipulating device is optionally selected, at block 406. In some embodiments, a LAA isolator, for example LAA isolator 326 shown in FIG. 3, is selected, for example according to the width of the LAA opening assessed at block 404. In some embodiments, a LAA isolator that has an expandable cover, for example expandable cover 328 shown in FIG. 3, that has a maximal width which is larger than the LAA opening, is selected.

According to some exemplary embodiments, a LAA closure device, for example a guide instrument having a working channel is transseptally introduced into the LA, at block 408. In some embodiments, a distal end of the guide instrument, for example guide instrument 302 shown in FIG. 3, is introduced, for example transseptally into the LA.

According to some exemplary embodiments, the LAA is optionally isolated from the LA, at block 410. In some embodiments, the LAA is optionally isolated using an LAA isolator for example LAA isolator 326 shown in FIG. 3. In some embodiments, the LAA is optionally isolated from the LA by placing an isolating cover, for example distal cover 328, surrounding a distal opening of a suction channel of the LAA isolator, over the LAA opening in the LA and in contact with the LA wall. In some embodiments, isolating the LAA, for example prior to and during LAA manipulation, allows to prevent entry of particles, for example blood clots, into the LA and into the blood stream.

According to some exemplary embodiments, vacuum is optionally applied on LAA lumen, at block 410. In some embodiments, the vacuum is optionally applied via the suction tube of the LAA isolator, for example when the isolating cover is at least partly in contact with the LA wall around the LAA opening.

According to some exemplary embodiments, a suction tube of the LAA closure device is introduced into the LAA, at block 412. In some embodiments, a distal end of the suction tube, for example suction tube 308 shown in FIG. 3, extends out from the working channel of the guiding instrument, and enters through the LAA opening into the LAA. In some embodiments, a distal end of the suction tube expands within the LA or within the LAA. In some embodiments, the suction tube extends out from the working channel and is navigated within the LAA using a control unit located outside the body.

According to some exemplary embodiments, a distal end of the suction tube is placed in contact with the LAA wall, at block 414. In some embodiments, the distal end of the suction tube, for example distal tip 312 shown in FIG. 3, is placed at least partly in contact with the LAA wall. Optionally, the suction tube distal end is soft and/or flexible, for example not to cause damage to the LAA wall. Optionally, the suction tube distal end expands and contacts the LAA wall in an expanded state.

According to some exemplary embodiments, a portion of the LAA wall is inverted into the suction tube, at block 416. In some embodiments, vacuum applied through the suction tube on the LAA wall inverts the LAA wall portion into the suction tube. In some embodiments, the LAA wall is inverted up to a distance of 1 cm, for example up to a distance of 0.8 cm, 0.5 cm or any intermediate, smaller or larger value, into the suction tube. In some embodiments, the LAA wall is inverted into the suction tube while the suction tube distal end is placed at least partly in contact with the LAA wall.

According to some exemplary embodiments, at least one grasper is attached to the inverted LAA wall, at block 418. In some embodiments, the at least one grasper, for example grasper 314 show in FIG. 3, is advanced over the suction tube and the suction tube distal end contacting the LAA wall. Alternatively, the at least one grasper is advanced within the suction tube to the inverted portion of the LAA wall. In some embodiments, the at least one grasper comprises a loop, for example a suture loop or a lasso which is placed around the inverted LAA wall. In some embodiments, the loop is tightened around the inverted LAA wall. In some embodiments, the grasper is attached to the inverted LAA wall, while the LAA wall is held by the suction tube, for example by the vacuum force applied on the LAA wall. Optionally, after the LAA wall is held by the grasper, the suction tube is disconnected from the LAA and moved into the working channel.

According to some exemplary embodiments, the LAA is invaginated using the grasper, at block 420. In some embodiments, the LAA is invaginated at least partly into the LA through the LAA opening, using the grasper. In some embodiments, the LAA is invaginated by moving, for example retracting, the grasper into the working channel while the grasper is attached to, for example tightened around, a portion of the LAA wall. Optionally, the LAA is invaginated using the grasper and the suction tube that holds the LAA wall by applying vacuum on the LAA wall.

According to some exemplary embodiments, the LAA is optionally at least partly invaginated into a LAA isolator positioned over the LAA opening in the LA, at block 422. In some embodiments, the LAA isolator is used as a LAA reshaper, configured to reshape a portion of the LAA invaginated into the LAA reshaper. Alternatively, the LAA is optionally at least partly invaginated into a LAA reshaper at block 422. In some embodiments, the LAA reshaper is configured to reshape a portion of the LAA invaginated into the LAA reshaper, for example without isolating the LAA from the LA.

According to some exemplary embodiments, the invaginated LAA is closed at blocks 424 and 426. In some embodiments, at least one ligator is attached, for example irreversibly attached, to the invaginated LAA, for example to prevent re-formation of a LAA lumen. In some embodiments, the at least one ligator is attached to the invaginated LAA while the invaginated LAA is held by the at least one grasper.

According to some exemplary embodiments, the at least one ligator, for example a loop, is positioned around the invaginated LAA, at block 424. In some embodiments, the loop, for example a closure loop is placed around a base of the invaginated LAA within the LA. In some embodiments, the loop is optionally placed around the invaginated LAA, while the invaginated LAA is held within the LAA isolator and/or within the LAA reshaper.

According to some exemplary embodiments, the at least one ligator, for example the loop is tightened around the invaginated LAA, at block 426. In some embodiments, the loop is optionally irreversibly tightened around the invaginated LAA.

According to some exemplary embodiments, the at least one grasper is optionally released from the invaginated LAA, at block 428. In some embodiments, the at least one grasper is released from the invaginated LAA, optionally after tightening of the loop at block 426. In some embodiments, after the release of the grasper from the invaginated LAA, the grasper is removed from the body.

Alternatively, the grasper is irreversibly attached to the invaginated LAA. In some embodiments, the LAA closure device disconnects from the grasper, leaving the grasper attached to the invaginated LAA.

According to some exemplary embodiments, the LAA closure device is disconnected from the closure loop, at block 430. In some embodiments, the LAA closure device is disconnected from the closure loop after the closure loop is tightened to the invaginated LAA. In some embodiments, the LAA closure device is disconnected from the closure loop by cutting a string or a wire between the LAA closure device and the loop.

According to some exemplary embodiments, the LAA closure device is retracted form the body, at block 432. In some embodiments, the LAA closure device is retracted from the body while leaving the invaginated LAA within the LA closed by the closure loop. Optionally, the invaginated LAA is closed by the closure loop and the grasper.

Exemplary LAA Invagination Using Loop

According to some exemplary embodiments, the LAA is at least partly or entirely invaginated into the LA, using a loop tightened around an inverted portion of the LAA wall. Reference is now made to FIGS. 5A-5I, depicting LAA invagination using a loop, according to some exemplary embodiments of the invention.

Figures 5A, 5B:
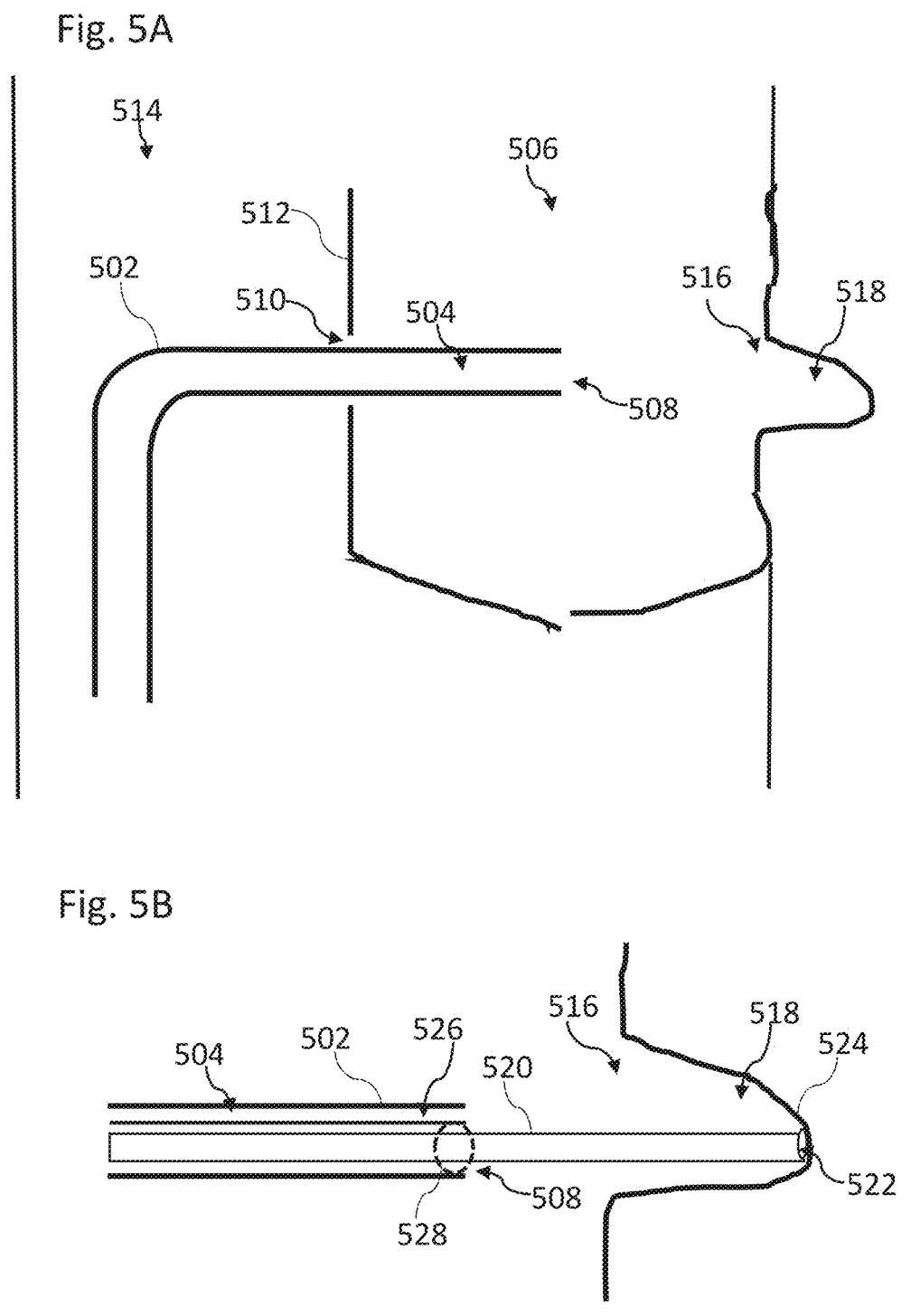

According to some exemplary embodiments, for example as shown in FIG. 5A, an elongated hollow guide instrument 502 is introduced into the LA 506. In some embodiments, the guide instrument 502 has an inner working channel terminating with a distal opening, for example opening 508. In some embodiments, the guide instrument is transseptally introduced into the LA 506, through an opening 510 in a septum 512 of the heart. In some embodiments, the guide instrument 502 is introduced into the LA from the right atrium (RA) 514.

According to some exemplary embodiments, the guide instrument 502, for example a distal section of the guide instrument 502 is navigated within the LA 506 towards a LAA opening 516 of the LAA 518. In some embodiments, the guide instrument 502 is navigated within the LA 506, to place a distal opening 508 in close proximity of up to 3 cm, for example up to 4 cm, up to 3 cm or any intermediate, smaller or larger value from the LAA opening 516.

According to some exemplary embodiments, for example as shown in FIG. 5B, a suction channel 520 terminating with a distal opening 522 extends out from the working channel 504 and into the LAA 518. In some embodiments, the suction channel 520 extends out from the suction channel distal opening, and through the LAA opening 516 into the LAA 518. In some embodiments, the suction channel 520 extends into the LAA, for example to place the suction channel distal opening 522 in contact with the LAA wall 524. Alternatively, the distal opening is placed at a distance of up to 1 cm, for example up to 0.7 cm, up to 0.5 cm, up to 0.2 cm or any intermediate, smaller or larger distance from the LAA wall 524.

According to some exemplary embodiments, at least one grasper 526, coupled to the suction channel 520 is optionally advanced within the working channel 504 towards the distal opening. In some embodiments, the at least one grasper 526 comprising loop is advanced over the suction channel 520. In some embodiments, when the suction tube distal opening 522 is within the LAA 518, the at least one grasper 526, for example loop 528 is advanced into the LA.

Figures 5C, 5D, 5E:
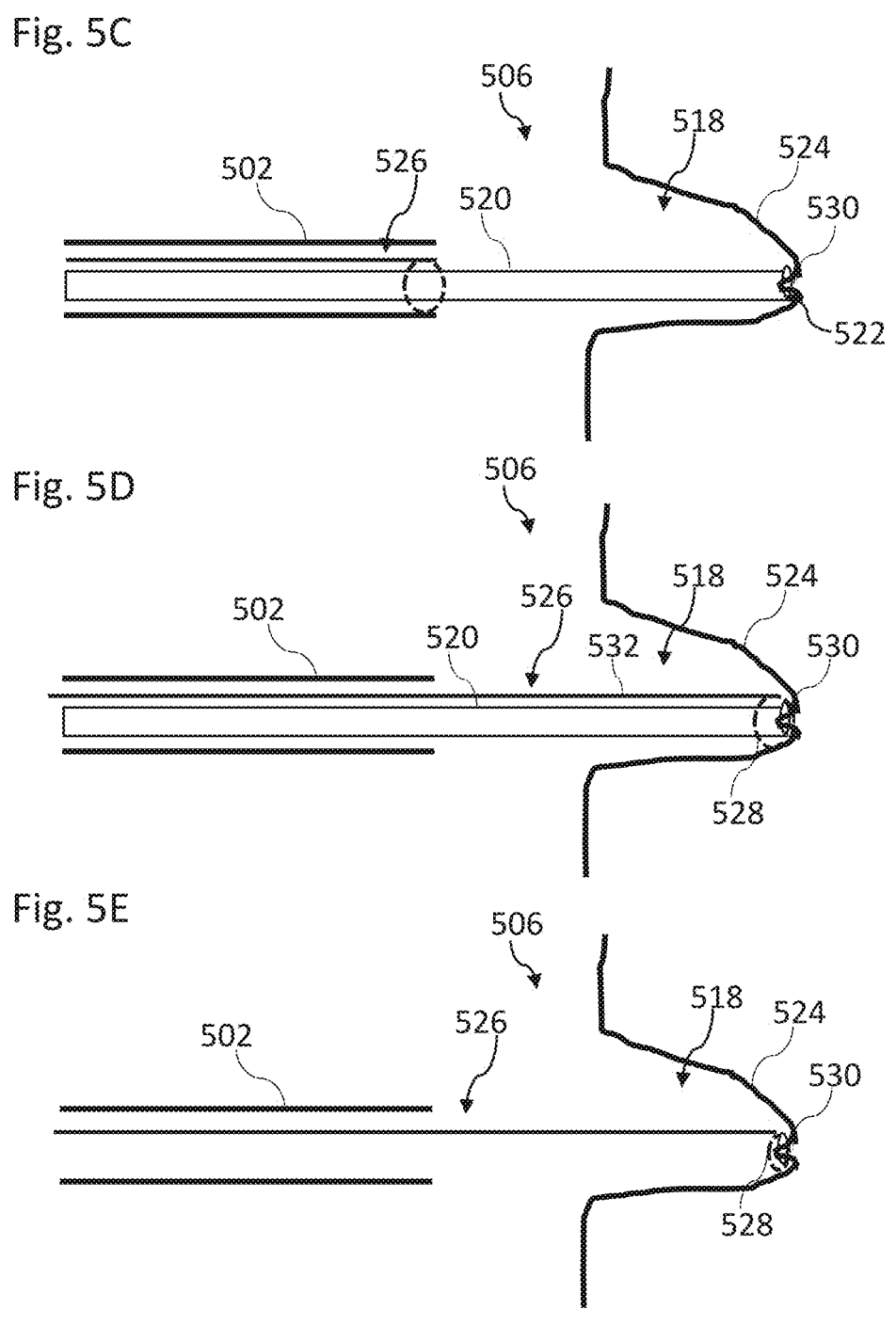

According to some exemplary embodiments, for example as shown in FIG. 5C, vacuum is applied via the suction channel 520 on the LAA wall 524 by the suction channel distal opening 522. In some embodiments, vacuum is applied on a portion of the LAA wall contacting a distal end of the suction tube. Alternatively, vacuum is applied on a portion of the LAA wall located at a distance of up to 1 cm from the suction tube distal opening 522. In some embodiments, for example as shown in FIG. 5C, the applied vacuum inverts a portion of the LAA wall into the suction channel 520, for example through the distal opening 522.

According to some exemplary embodiments, for example as shown in FIG. 5D, the at least one grasper 526 is advanced towards the LAA wall 524. In some embodiments, the at least one grasper 526 is advanced over the suction channel 520 towards the suction channel distal opening 522. In some embodiments, a loop 528 of the at least one grasper 526 is placed around a base of the inverted LAA 530 while the inverted LAA 530 is held within the suction channel 520, for example by the applied vacuum. In some embodiments, the loop 528 is advanced over the suction channel using a shaft 532, for example a flexible shaft, connected to the loop. In some embodiments, the shaft is bendable. In some embodiments, the loop 528 is tightened around the inverted LAA wall 530, optionally while vacuum is applied. In some embodiments, the loop 528 is tightened around the inverted LAA wall by movement of the shaft 532, for example by rotation and/or retraction of the shaft.

According to some exemplary embodiments, for example as shown in FIG. 5E, once the inverted LAA 530, for example the inverted LAA wall, is held by the at least one grasper, for example the loop 528 of the grasper, the suction channel 520 is optionally retracted into the working channel 502. Alternatively, the suction remains in contact with the LAA wall while the loop 528 is placed around the inverted LAA 530.

Figures 5F, 5G, 5H, 5I:
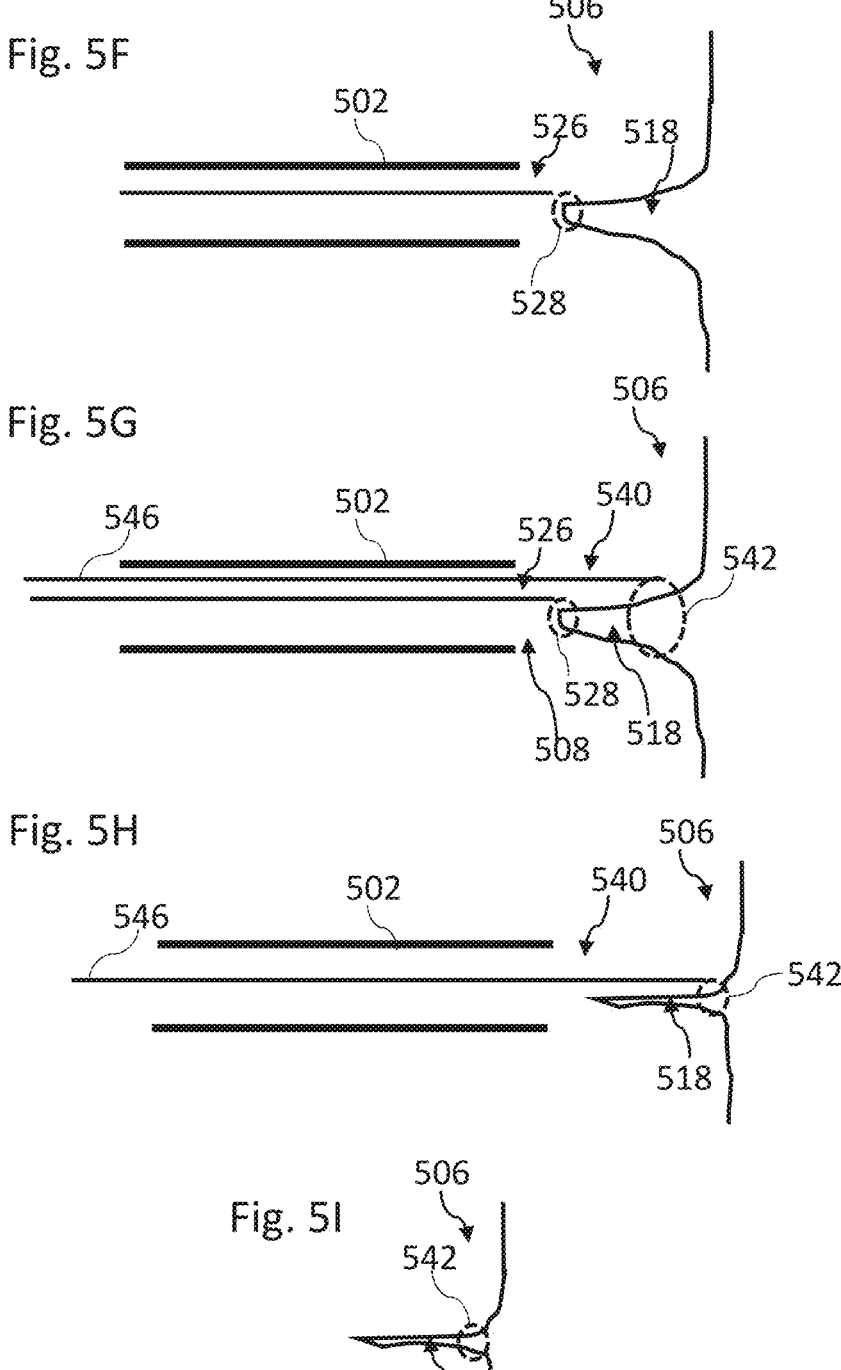

According to some exemplary embodiments, for example as shown in FIG. 5F, the LAA 518 is inverted at least partly or entirely into the LA using the at least one grasper. In some embodiments, the at least one grasper is moved into the working channel 502 while being in contact with the LAA, for example with a previously inverted portion of the LAA wall, for example inverted LAA 530. Optionally, the LAA 518 is at least partly or entirely inverted into the LA using the at least one grasper and the suction tube that is kept in contact with the LAA wall. In some embodiments, the LAA is inverted into the LA while vacuum is applied on the LAA wall by the suction channel.

According to some exemplary embodiments, for example as shown in FIG. 5G, at least one ligator, for example ligator 540 is attached to the invaginated LAA 518. In some embodiments, a loop 542 of the ligator 540 is optionally placed around the invaginated LAA 528. In some embodiments, the at least one ligator 540 is advanced within the working channel 502 towards the working channel distal opening 508, optionally over the grasper 526. In some embodiments, the ligator 540, for example a loop 542 of the ligator 540, is advanced distally to the grasper 526, for example distally to the loop 528 of the grasper 526. In some embodiments, the ligator 540, for example a loop 542 of the ligator 540, is advanced over the grasper 526, for example over the loop 528 of the grasper 526.

According to some exemplary embodiments, the loop 542 is advanced towards a base of the invaginated LAA and is optionally placed around a base of the invaginated LAA within the LA 506. In some embodiments, the ligator 540 is advanced within the working channel, for example towards the LAA wall using a shaft 546, for example a bendable shaft. In some embodiments, the shaft 546 is connected to the loop 542.

According to some exemplary embodiments, for example as shown in FIG. 5H, the ligator 540, for example the loop 542 of the ligator 540, is tightened around the invaginated LAA 518. In some embodiments, the loop 542 is irreversibly tightened around the invaginated LAA 518. In some embodiments, the loop 542 is tightened around the invaginated LAA by manipulation of the shaft 546, for example by moving and/or rotating of the shaft 546. In some embodiments, tightening of the loop 542, for example using the shaft 546, disconnects the loop 542 from the shaft 546. In some embodiments, when the loop 542 is tightened to the invaginated LAA, the grasper 526 disconnects from the invaginated LAA and is retracted into the working channel 502. Optionally or additionally, a suction channel connected to the invaginated LAA is retracted into the working channel 502 after the attachment of the ligator 540, for example loop 542 to the invaginated LAA 518.

According to some exemplary embodiments, for example as shown in FIG. 5I, after the attachment, for example irreversibly attachment or tightening of the ligator, for example the ligator loop 542 to the invaginated LAA, the working channel 502 is removed from the LAA. In some embodiments, attachment of the ligator, for example tightening of the ligator around the invaginated LAA, closes the LAA. In some embodiments, the ligator irreversibly closes the LAA. In some embodiments, after LAA closure the invaginated LAA is positioned within the LA. Optionally, over time, a volume and/or size of the closed invaginated LAA 518 is reduced.

Figures 6A, 6B:
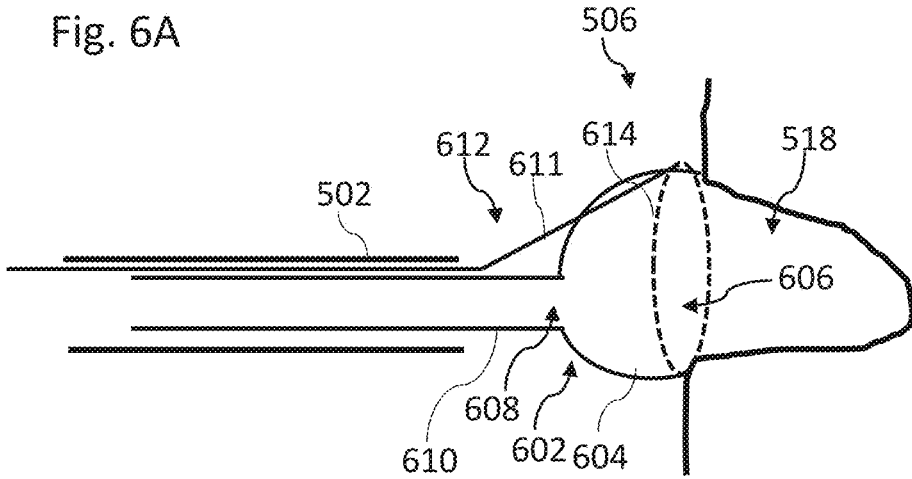
FIGS. 6A-6H are schematic illustration of a process for closure of the LAA using a LAA isolator, according to some exemplary embodiments of the invention.

According to some exemplary embodiments, for example as shown in FIG. 6A, a LAA isolator 602 is advanced within the working channel 502 and expanded in the LA 506, prior to and/or during penetration of the LAA closure device into the LAA. In some embodiments, the LAA isolator 602 comprises a cover, for example a cup 604. In some embodiments, the cup 604 is an expandable cup configured to travel within the working channel 502 in a collapsed state and to expand within the LA 506. In some embodiments, a distal edge of the cup is placed in contact with a LA wall surrounding the LAA opening. In some embodiments, a distal opening 606 of the cup faces the LAA opening, and a proximal opening 608 of the cup 604 is connected to a channel 610, for example a suction channel, of the LAA isolator 602. In some embodiments, the LAA isolator comprises a channel 610, for example a suction channel terminating with a distal opening in the cup 604, and a proximal opening located outside the heart, for example outside the body.

According to some exemplary embodiments, the LAA isolator 602 isolates the LA 506 from the LAA 518 by generating a direct flow path between the LAA 518 and outside the body. In some embodiments, isolation of the LA 506 from the LAA 518 allows, for example to prevent flow of particles from the LAA 518 into the LA 506 and the blood stream.

According to some exemplary embodiments, at least one ligator, for example ligator 612 is coupled at least partly to the LAA isolator. In some embodiments, a loop of the ligator, for example loop 614 is coupled to the inner or outer surface of the cup 604. In some embodiments, the loop 614 is coupled to the cup 604 at a distance of up to 4 cm, for example up to 3 cm, up to 2 cm, up to 1 cm, up to 0.5 cm or any intermediate, smaller or larger value from the distal opening 606 of the cup 604. In some embodiments, the loop 614 surrounds the opening 606. In some embodiments, the ligator comprises a shaft 611, for example a flexible shaft, connected to the loop 614. In some embodiments, the ligator shaft 611 is configured to control the attachment or tightening of the loop 614 around tissue positioned within loop 614. In some embodiments, movement of the ligator shaft 611, for example retraction and/or rotation, tightens the loop. Optionally, tightening of the loop 614 decouples the loop 614 from the cup 604. Additionally, or optionally, tightening of the loop disconnects the ligator shaft 611 from the loop 614. According to some exemplary embodiments, for example as shown in FIG. 6B, the suction channel 520 travels within the LAA isolator channel 610 and extends through the distal opening 606 of the cup 604 into the LAA 518.

Figure 6C:
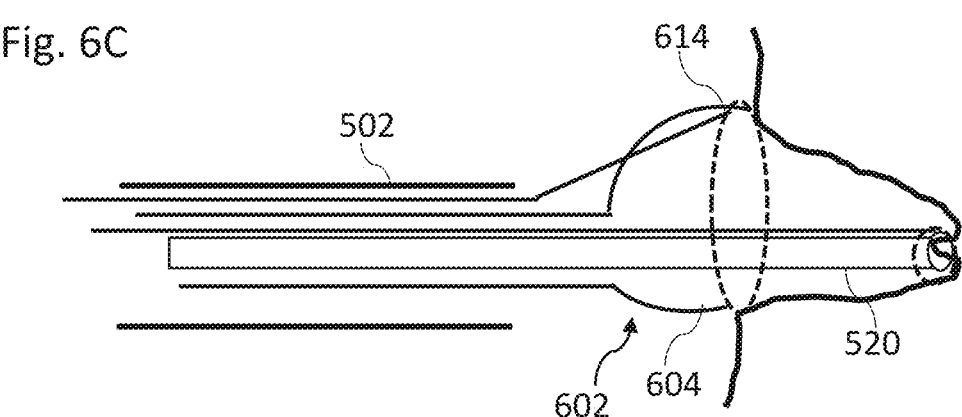
Figure 6D:
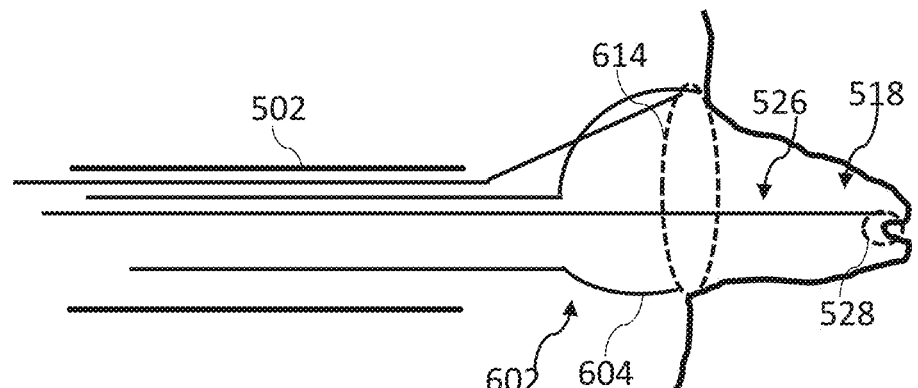

According to some exemplary embodiments, the LAA isolator 602 isolates the LA from the LAA during the inversion, for example partial inversion of the LAA into the suction tube, for example as described in FIG. 6C and in FIG. 5C, attaching the grasper to the inverted LAA, for example as described in FIGS. 6C, 6D, 5D and 5E.

Figure 6E:
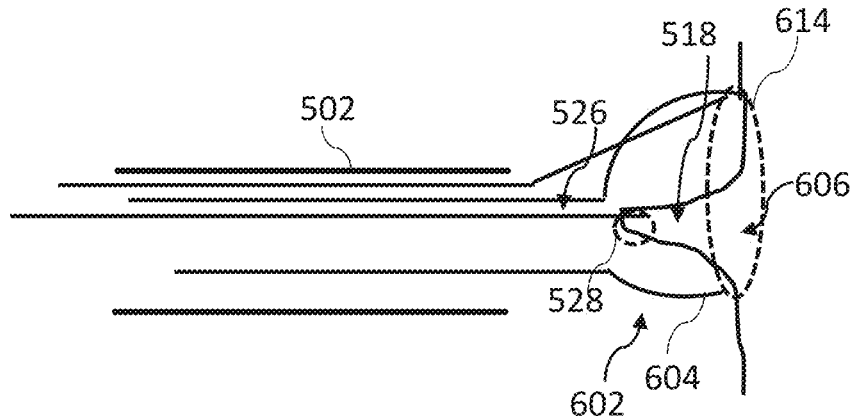

According to some exemplary embodiments, for example as shown in FIG. 6E, the LAA is at least partly invaginated into the cup 604 of the LAA isolator 602, for example through the cup distal opening 606. In some embodiments, the LAA is invaginated into the cup 604, while the cup, for example a distal edge of the cup surrounding the distal opening 606 is in contact with the LA wall around the LAA opening. In some embodiments, the LAA 518 is invaginated into the cup 604 to a distance larger than 0.5 cm, for example larger than 1 cm, larger than 1.5 cm, larger than 2 cm or any intermediate, smaller or larger distance from the distal opening 606. In some embodiments, the LAA 518 is invaginated into the cup 604 to a distance that allows attachment of the ligator, for example the ligator loop 614 around the invaginated LAA. In some embodiments, the LAA is invaginated using the grasper 526 into the ligator loop 614.

Figures 6F, 6G, 6H:
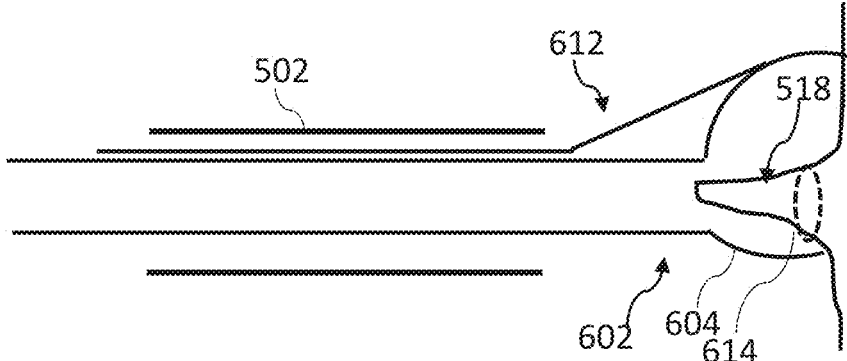

According to some exemplary embodiments, for example as shown in FIG. 6F, the loop is attached and/or tightened around the invaginated LAA 518, for example around a base of the invaginated LAA 518. In some embodiments, for example as shown in FIG. 6F, tightening of the loop 614 decouples the loop 614 from the LAA isolator cup 604. Optionally or additionally, tightening of the loop 614 disconnects ligator shaft 611 from the loop 614. In some embodiments, for example as shown in FIG. 6F, the loop 614 is tightened around the invaginated LAA 518, while the invaginated LAA 518 is held by the grasper 526, for example by the grasper loop 528.

According to some exemplary embodiments, for example as shown in FIG. 6G, once the ligator is attached to the invaginated LAA, for example once the ligator loop 614 is tightened around the invaginated LAA 518, the grasper is optionally disconnected from the LAA and is retracted from the heart via the working channel. Alternatively, the grasper loop is irreversibly attached to the LAA and disconnects from the grasper shaft.

According to some exemplary embodiments, for example as shown in FIG. 6H, once the invaginated LAA is closed, for example by at least one ligator, the LAA isolator 602 disconnects from the LA wall, and is retracted from the heart via the working channel 502. Additionally, during the retraction of the LAA isolator, the cup 604 is collapsed into the working channel 502.

According to some exemplary embodiments, during the attachment of the LAA isolator cup, for example cup 604 to the LA wall around the LAA opening, vacuum is applied via the suction channel of the LAA isolator. In some embodiments, the vacuum is applied continuously or intermittently.

According to some exemplary embodiments, during the at least partial invagination of the LAA into the cup 604, the invaginated LAA is reshaped, for example by a reshaper located within the cup 604. In some embodiments, the reshaping of the invaginated LAA prior to the attachment of the ligator to the invaginated LAA, allows for example to modify at least one of a volume, shape and size of the invaginated LAA, for example to better fit a ligator to the invaginated LAA or to reduce a footprint of the closed invaginated LAA in the LA.

Exemplary LAA Manipulation System

Figures 7A, 7B:
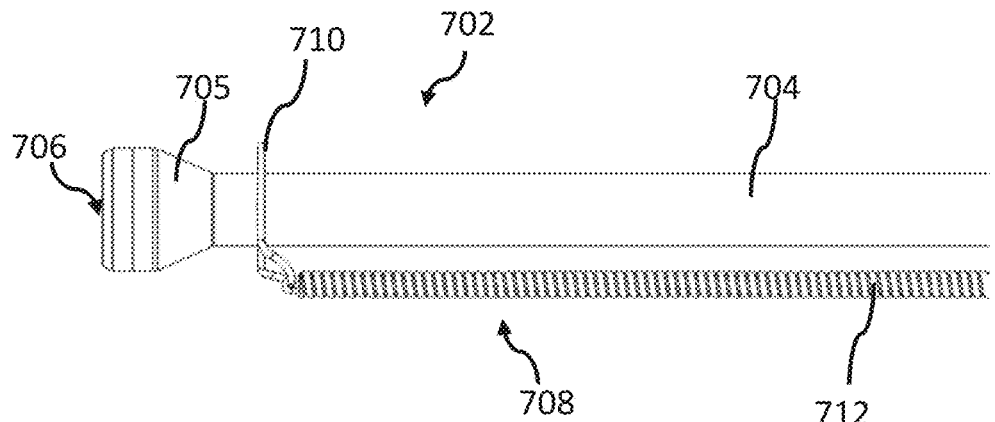
FIG. 7A is an image of a suction tube and a tissue grasper, which are optionally part of a LAA closure system, according to some exemplary embodiments of the invention.
FIG. 7B is an image of a ligator coupled to a LAA isolator, for example a LAA reshaper, which are optionally part of a LAA closure system, according to some exemplary embodiments of the invention.

Reference is now made to FIG. 7A depicting a suction tube and a grasper, according to some exemplary embodiments of the invention.

According to some exemplary embodiments, an elongated tubular body, for example a suction tube 704 comprises a distal end 705, for example a suction cup, shaped and sized to penetrate into the LAA, and a proximal end, optionally connectable to a vacuum source, for example by a connector located at the proximal end. In some embodiments, the suction tube 704 terminates with a distal opening 706, at the distal end 705. In some embodiments, the suction tube 704 is bendable, for example to allow navigation into the LAA within a working channel of a guiding tool, for example a catheter. In some embodiments, a distal section of the suction tube 704 shaped and sized to penetrate into the LAA has an outer diameter or an outer width in a range of about 0.7 mm to 17 mm, for example about 1 mm to about 10 mm, about 1 mm to about 15 mm, about 1 mm to about 5 mm, about 3 mm to about 10 mm, about 5 mm to about 15 mm or any intermediate, smaller or larger range of values.

According to some exemplary embodiments, a distal opening 706 of the suction cup has a maximal width in a range of about 3 mm-13 mm, for example 3 mm-6 mm, 5 mm-8 mm, 7 mm-12 mm or any intermediate, smaller or larger range of values. Optionally, the suction cup is an expandable suction cup configured to expand when said elongated tubular body extends out from the catheter, and to collapse within said catheter According to some exemplary embodiments, at least one grasper, for example grasper 708 comprises a distal loop, for example a snare 710, and a proximal shaft 712, for example a bendable shaft, connected to the snare 710. In some embodiments, for example as shown in FIG. 7A, the grasper 708, for example the snare 710 is shaped and sized to surround the suction tube 704. In some embodiments, the suction tube 704 passes within the snare 710. In some embodiments, a maximal width of the loop 710, for example when the loop is in an open state, is larger than a maximal width of the suction tube 704 and/or a distal end 705 of the suction tube. According to some exemplary embodiments, the snare 710 is configured to move over the suction tube

704, for example by movement of the shaft 712, for example axial movement of the shaft 712. Additionally, the snare 710 is configured to move between an open loose state and a tightened state by movement, for example axial and/or rotational movement, of the shaft 712. In some embodiments, the snare 710 is formed from at least one of Polyurethane, Polytetrafluoroethylene (PTFE), polyethylene (Pet), Polyvinylidene fluoride or polyvinylidene difluoride (PVFD), Polyetheretherketone (PEEK), Nitinol, and/or perfluoroalkoxy (PFA). In some embodiments, the snare comprises a metal wire, for example brass wire, for example to allow tracking of the snare. In some embodiments, the suction tube distal end 704 is formed from at least one of PEEK, PTFE, Pet, PVFD, Nitinol, and/or PFA.

According to some exemplary embodiments, the suction tube 704 and the grasper 708 are part of a LAA invaginator 702, which is configured to penetrate into the LAA, grasp a portion of the LAA wall and invaginate the LAA using the grasped LAA wall portion, at least partly into the LA.

Reference is now made to FIG. 7B depicting a ligator coupled to a LAA isolator, for example a LAA reshaper, according to some exemplary embodiments of the invention.

According to some exemplary embodiments, a LAA isolator, for example isolator 716 comprises a channel 718 terminating with a distal cup 720 having a distal opening 726. In some embodiments, the cup 720 is formed from a wire mesh 722 and a sheet layer 724 coupled to the wire mesh 722. In some embodiments, a distal edge 728 of the cup 720 is configured to be attached to a wall of the LA, for example around a LAA opening. In some embodiments, the distal edge 728 is soft and/or flexible, for example not to cause substantial damage, for example tearing or perforation, to the LA wall tissue.

According to some exemplary embodiments, the cup is made from a wire mesh, for example a wire frame, covered by polyurethane. Optionally, the wire frame is formed from Nitinol. In some embodiments, the wire mesh, for example wire mesh 722 comprises a plurality of springs positioned around the distal opening 726, configured to contact and/or to fit LAA openings with different opening sizes, for example different widths. In some embodiments, the wire mesh 722 comprises a plurality clips, for example nitinol clips, surrounding the distal openings 726, and configured to hold the loop 732 and to allow rapid release of the loop 732.

According to some exemplary embodiments, the cup 720 is expandable, configured to move between a collapsed state within a working channel to an expanded state when extending from an opening, for example a distal opening of the working channel. In some embodiments, the sheet material 724 is sealed to fluids. Alternatively, the sheet material 724 comprises pores that are shaped and sized to allow passage of liquid, for example blood, and is sealed to particles, for example blood clots and tissue debris. In some embodiments, a width of the pores is in a range of about 3 mm to about 35 mm, for example about 5 mm to about 30 mm, about 5 mm to about 10 mm, about 7 mm to about 15 mm, about 10 mm to about 20 mm or any intermediate, smaller or larger range of values. In some embodiments, the cup 720 forms a sealed flow path for the particles between the distal opening 726 and the channel 718 lumen. In some embodiments, the wire mesh 722 is formed from a shape memory alloy, for example Nitinol configured to expand the cup 720 in a relaxed state.

According to some exemplary embodiments, at least one ligator, for example ligator 730 is coupled at least partly to the LAA isolator 716. In some embodiments, the ligator 730 comprises a loop 732, for example a suture loop, attached, for example reversibly attached to the cup 720. In some embodiments, the loop 732 is attached to an inner surface of the cup 720. Alternatively, the loop 732 is attached to an outer surface of the cup 720. In some embodiments, the loop 732 is attached to the cup, for example to the wire mesh 722 or to the sheet layer 724. In some embodiments, the loop 732 surrounds the distal opening 726, and is positioned at a distance of up to 3 cm, for example up to 1 cm, up to 0.5 cm or any intermediate, smaller or larger distance from the distal opening 726 of the cup 720. In some embodiments, the loop 732, for example a snare suture, is made from non-absorbable silk, for example non absorbable or absorbable silk #0 or #1. Alternatively, the loop 732 is made from at least one of Nylon, PTFE, expanded Polytetrafluoroethylene (EPTFE). In some embodiments, the loop 732 has a maximal width or a maximal diameter in a range of about 5 mm to about 17 mm, for example 5 mm to 10 mm, 8 mm to 12 mm, 10 mm to 17 mm or any intermediate, smaller or larger range of values.

According to some exemplary embodiments, the loop 732 is coupled to a shaft 734 or a sleeve. In some embodiments, the shaft 734 is coupled at least partly to the channel 718. In some embodiments, the shaft 734 is coupled at least partly to an outer surface of the channel 718. Alternatively, shaft 734 travels within the channel 718. In some embodiments, the shaft 734 is a hollow sleeve and comprises an inner lumen. In some embodiments, a suture connected to the loop 732 or forming the loop 732 passes within the sleeve 734. In some embodiments, axial movement of the wire, for example retraction of the suture, tightens the loop 732, for example irreversibly tightens the loop 732 around tissue located within the cup 720. Optionally, axial movement of the suture, for example retraction of the suture, detaches the loop 732 from the cup 720, and optionally disconnects the loop 732 from the suture and/or the sleeve 734.

According to some exemplary embodiments, movement of the shaft 734, for example axial movement and/or rotation of the shaft 734 tightens, for example reversibly tightens the loop 732 around tissue located within the cup 720. Optionally, axial movement and/or rotation of the shaft 734, detaches the loop 732 from the cup 720, and optionally disconnects the loop 732 from the shaft 734 and/or from the suture within the shaft 734.

Figure 7C:
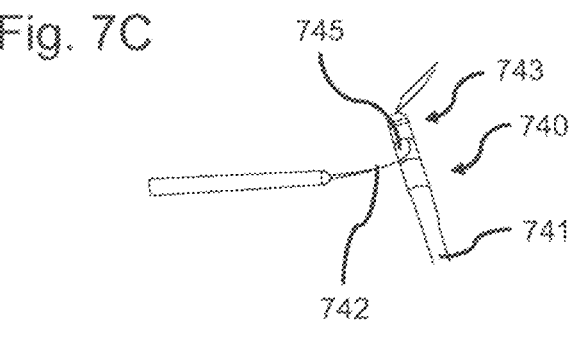
FIG. 7C is an image of a suture cutter which is optionally part of a LAA closure system, according to some exemplary embodiments of the invention.
Figure 7D:
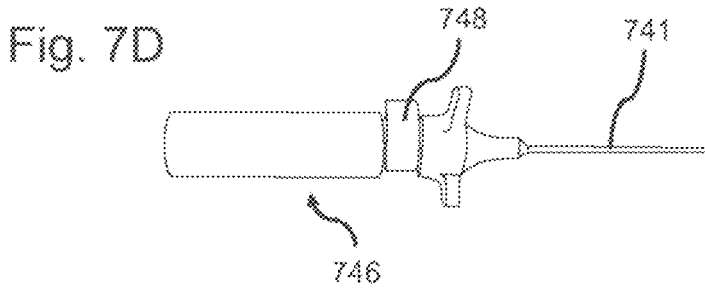
FIG. 7D is an image of a control handle of the suture cutter shown in FIG. 7C, according to some exemplary embodiments of the invention.

According to some exemplary embodiments, for example as shown in FIG. 7C, a system for LAA closure comprises a cutter, for example a suture cutter 740. In some embodiments, the cutter comprises an elongated body 741 having a distal end 743 comprising a slot 745, through which a suture 742 passes. In some embodiments, the elongated body 741 is connected to a handle 746, for example as shown in FIG. 7D. In some embodiments, the cutter distal end 742 comprises a movable cutter configured to move within the slot 745. In some embodiments, movement of the movable cutter 745 cuts a section of suture 742 located within the slot 745. In some embodiments, the distal end 742 comprises at least one radiopaque marker, for example to allow visualization of the distal end 742 from outside the body, optionally by x-ray visualization.

According to some exemplary embodiments, the handle 746 controls the movement of the movable cutter within the slot 745. In some embodiments, the handle 746 comprises a lock 746 configured to prevent the movement of the movable cutter.

Figure 7E:
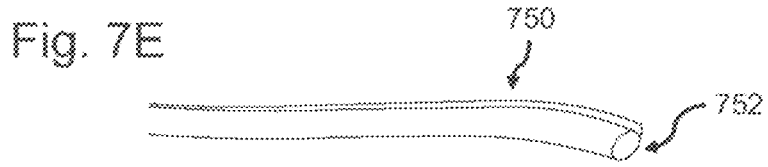
FIG. 7E is an image of a guiding tube, for example a guiding device, which is optionally part of a LAA closure system, according to some exemplary embodiments of the invention.
Figure 7F:
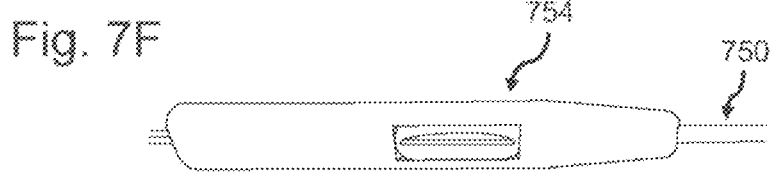
FIG. 7F is an image of a control handle of the guiding tube shown in FIG. 7E, according to some exemplary embodiments of the invention.
Figure 7G:
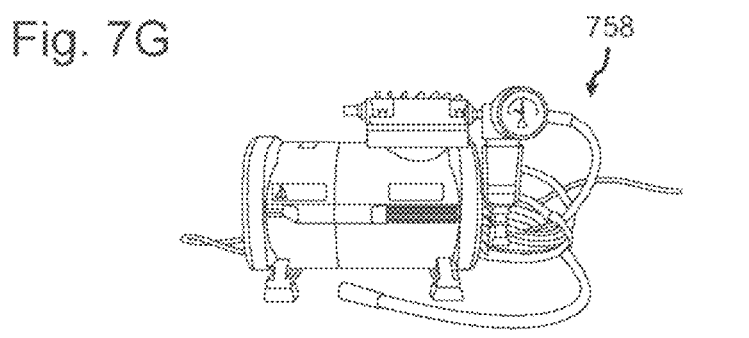
FIG. 7G is an image of a suction pump which is optionally connectable to a LAA closure system, according to some exemplary embodiments of the invention.

According to some exemplary embodiments, for example as shown in FIG. 7E, a system for LAA closure comprises an elongated steerable tube 750, having an inner working channel. In some embodiments, the tube 750 is a braided tube or sheath having a distal opening 752. In some embodiments, an outer diameter of the tube 750 is in a range of about 1.5 mm to about 15 mm, for example about 2 mm to about 10 mm, about 3 mm to about 8 mm, about 5 mm to about 12 mm, about 5 mm to about 15 mm or any intermediate, smaller or larger range of values. In some embodiments, the inner diameter or inner width of the working channel is in a range of about 1.5 mm to about 15 mm for example about 2 mm to about 10 mm, about 3 mm to about 8 mm, about 5 mm to about 12 mm, about 5 mm to about 15 mm or any intermediate, smaller or larger range of values. In some embodiments, a length of the tube 750 is in a range of 100 cm-20 cm, for example 100 cm-140 cm, 120 cm-160 cm, 110 cm-140 cm, or any intermediate, smaller or larger range of values. In some embodiments, the tube 750 or at least a distal portion of the tube located inside the heart is steerable. According to some exemplary embodiments, for example as shown in FIG. 7F, a proximal end of the tube 750 is coupled to a control handle 754. In some embodiments, the control handle 750 is configured to control the steering of the tube 750 within the body, for example within the heart, and/or the LAA. Additionally, or alternatively, the control handle 754 controls advancement and/or tightening of the grasper 708, for example the grasper loop 710. In some embodiments, the control handle 754 comprises a force limiter, for example to control the tightening of the grasper, for example the grasper loop 710. In some embodiments, the grasper loop is tightened with a maximal force in a range of about 3 Newton (N) to about 35 N, for example about 5 N to about 15 N, about 10 N to about 20 N, about 15 N to about 25 N, about 20 N to about 30 N or any intermediate, smaller or larger range of values.

Figure 7H:
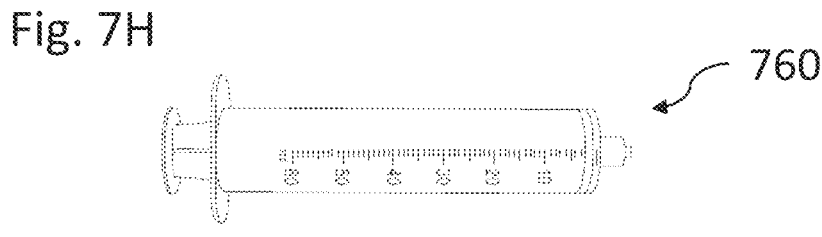
FIG. 7H is an image of a syringe which is optionally connectable to a LAA closure system, according to some exemplary embodiments of the invention.

According to some exemplary embodiments, for example as shown in FIG. 7F, the system for LAA closure is connectable to a vacuum source, for example pump 758 or to a syringe 760 shown in FIG. 7H. In some embodiments, the pump 758 or syringe 760 is connectable to the control handle 754. In some embodiments, the pump 758 or syringe 760 is used to apply vacuum on the LAA wall, for example to allow inversion of a portion of the LAA wall into the suction tube. In some embodiments, a level of vacuum applied on the LAA wall during convexing of the LAA wall is in a range of about 10 mmHG to about 780 mmHG, for example about 10 mmHG to about 100 mmHG, about 50 mmHG to about 200 mmHG, about 100 mmHG to about 300 mmHG, about 200 mmHG to about 500 mmHG, about 400 mmHG to about 780 mmHG or any intermediate, smaller or larger range of pressure levels.

According to some exemplary embodiments, the pump 758 or syringe 760 is used to apply vacuum, for example through the LAA isolator on the LAA, optionally to remove particles from the LAA into a suction channel of the LAA isolator. In some embodiments, a level of vacuum applied through the LAA isolator on the LAA is in a range of about 10 mmHG to about 780 mmHG, for example about 10 mmHG to about 100 mmHG, about 50 mmHG to about 200 mmHG, about 100 mmHG to about 300 mmHG, about 200 mmHG to about 500 mmHG, about 400 mmHG to about 780 mmHG or any intermediate, smaller or larger range of pressure levels.

Exemplary LAA Manipulation Using System

Reference is now made to FIGS. 8A-8E depicting LAA wall grasping, according to some exemplary embodiments of the invention.

Figure 8A:
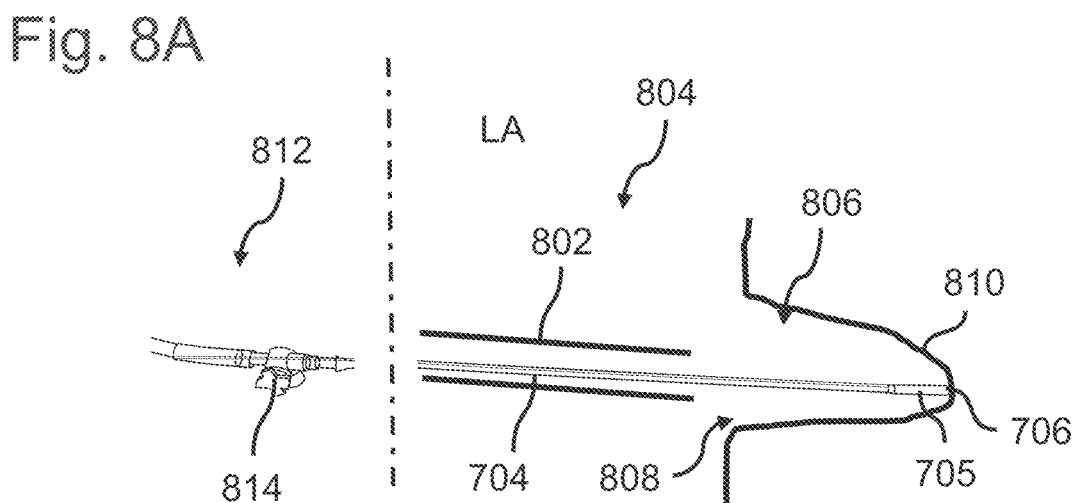

According to some exemplary embodiments, a working channel 802, for example a working channel of a guide instrument is introduced into the LA 804. In some embodiments, a suction channel, for example suction channel 704 extends out from a distal opening of the working channel 802, within the LA 804. In some embodiments, the suction channel 704 penetrates into the LAA 806, through the LAA opening 808 in the LA 804. In some embodiments, a suction channel distal opening, for example distal opening 706 is placed in contact or is placed at a distance smaller than 1 cm, for example smaller than 0.5 cm, smaller than 0.2 mm or any intermediate, smaller or larger distance from the LAA wall 810. In some embodiments, for example as shown in FIG. 8A, a proximal opening of the suction channel 704 is connected to a vacuum source, for example a pump or syringe located outside the body. In some embodiments, the suction channel 704 is connected to the vacuum source via at least one valve, for example valve 814. In some embodiments, valve 814 controls vacuum application through the suction channel 704.

Figure 8B:
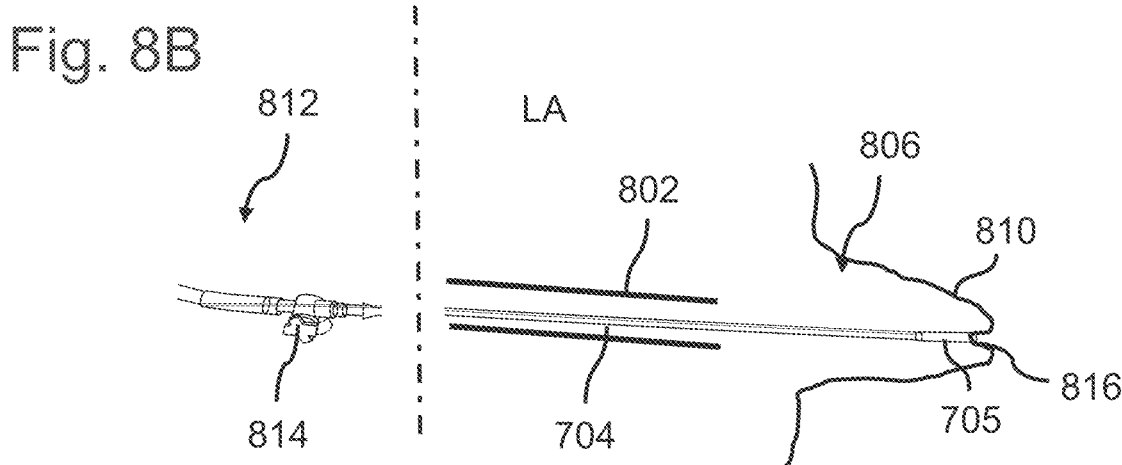
Figure 8C:
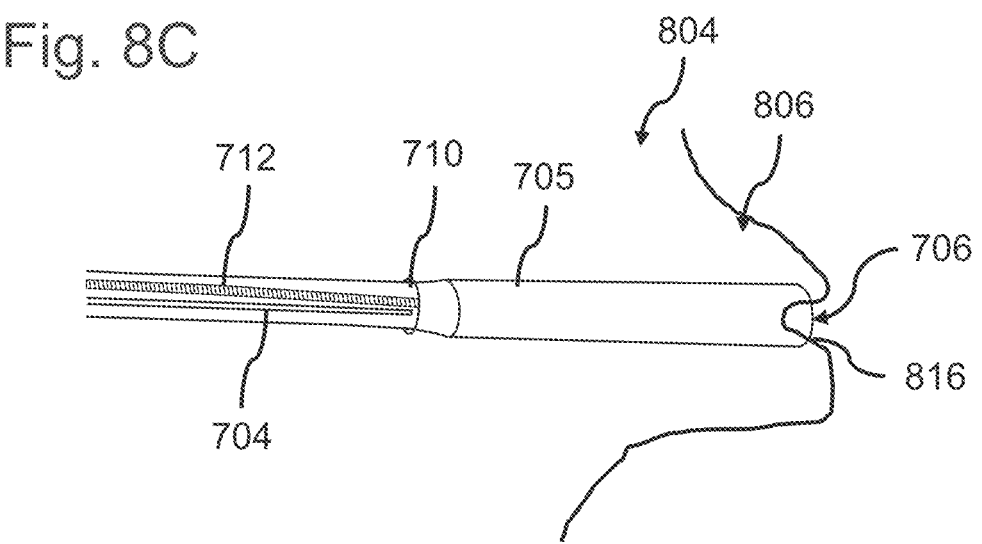

According to some exemplary embodiments, for example as shown in FIGS. 8B and 8C, when the distal opening 706 contacts the LAA wall or in proximity to the LAA wall, vacuum is applied via the suction channel 704 on the LAA wall 810. In some embodiments, the vacuum is applied by opening the at least one valve 814 located outside the body 812. In some embodiments, the applied vacuum inverts a portion of the LAA wall 810 into the suction tube 704, for example through the distal opening 706. In some embodiments, the inverted portion is a small portion of the LAA wall having a length of up to 2 cm, for example up to 1 cm, up to 0.5 cm, up to 0.2 cm or any intermediate, smaller or larger value.

According to some exemplary embodiments, for example as shown in FIG. 8D, the grasper, for example grasper 708 is advanced over the suction channel 704 towards the inverted LAA portion 816. In some embodiments, a loop 710 of the grasper 708 is advanced over the suction channel 704 to surround a base of the inverted LAA portion 816. In some embodiments, the loop 710 is tightened around the inverted LAA portion 816, for example around the base of the inverted LAA portion 816. In some embodiments, the loop 710 is optionally reversibly tightened around the inverted LAA 816.

According to some exemplary embodiments, for example as shown in FIG. 8E, once the inverted LAA 816 is held, for example grasped, by the loop 710, the suction channel 704 is retracted into the working channel. In some embodiments, vacuum application is stopped prior to the retraction of the suction channel, for example by closing the valve 814. Alternatively, application of vacuum continuous and the inverted LAA 816 is held both by the suction channel 704 and the grasper, for example by the tightened loop 710 of the grasper 708.

Reference is now made to FIGS. 8F-8I, depicting invagination of the LAA, according to some exemplary embodiments of the invention.

According to some exemplary embodiments, for example as shown in FIG. 8F, once an inverted LAA 816 is held by the grasper loop 710, a LAA isolator 716, for example a LAA reshaper is advanced towards the LAA opening 808 in the LA. In some embodiments, the LAA isolator 716 extends from the working channel into the LA. In some embodiments, a cup 720, for example an expandable cup, expands within the LA and advanced towards the LAA opening in the LA. In some embodiments, the LAA isolator 716 is advanced over the grasper towards the LAA opening 808.

According to some exemplary embodiments, for example as shown in FIG. 8G, the cup 720 is placed in contact with the LA wall 820 surrounding the LAA opening 808, for example to at least partly isolate the LAA from the LA. In some embodiments, the LAA isolator, for example cup 720 prevents flow of particles from the LAA into the LA. In some embodiments, vacuum is applied via the channel 718 and the cup 720 of the LAA isolator on the LAA 806, for example to draw particles from within the LAA 806 into the channel 718 and outside the body. In some embodiments, the LAA isolator initiates isolation of the LAA from the LA, prior to penetration of the suction channel 704 into the LAA 806, prior to the inversion of the LAA wall portion into the suction channel, prior to the tightening of the grasper loop around the inverted LAA or prior to or during the invagination of the LAA.

Figure 8H:
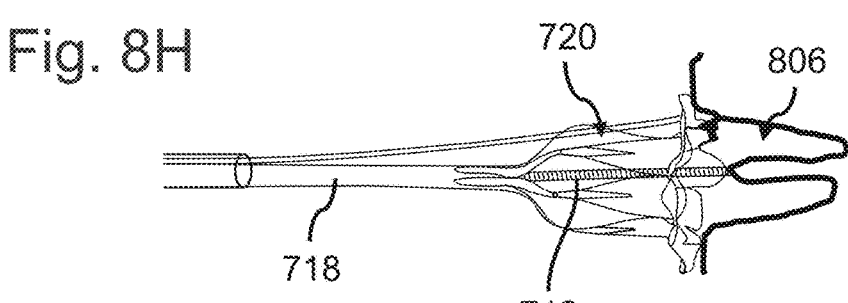

According to some exemplary embodiments, for example as shown in FIG. 8G, when the LAA isolator isolates the LAA from the LA, invagination of the LAA using the grasper initiates. Alternatively, the LAA isolator isolates the LAA from the LA during the invagination of the LAA using the grasper. In some embodiments, for example as shown in FIGS. 8G and 8H, the LAA is invaginated into the cup 720 by retracting the grasper, for example shaft 712 into the channel 718 and/or the working channel, while the loop 710 is tightened around the inverted LAA 816.

Figure 8I:
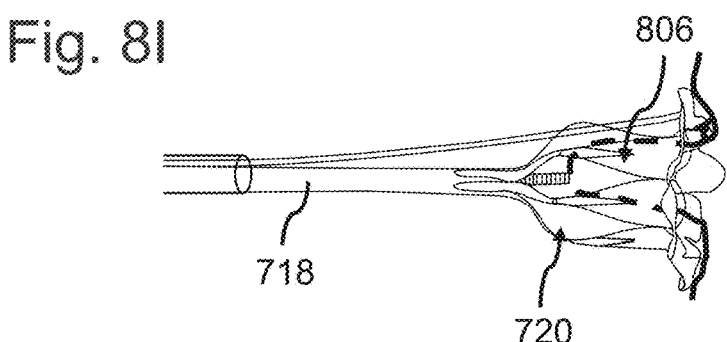

According to some exemplary embodiments, for example as shown in FIG. 8I, the LAA 806 is invaginated into the cup 720 of the LAA isolator 716. In some embodiments, the LAA 806 is invaginated at least partly into the cup 720, for example through the distal opening 726 of the cup 720. Optionally, for example as shown in FIG. 8I, the LAA 806 is entirely invaginated into the cup 720. In some embodiments, for example when a LAA isolator is not used, the LAA 806 is invaginated partly or entirely into the LA.

Figure 9A:
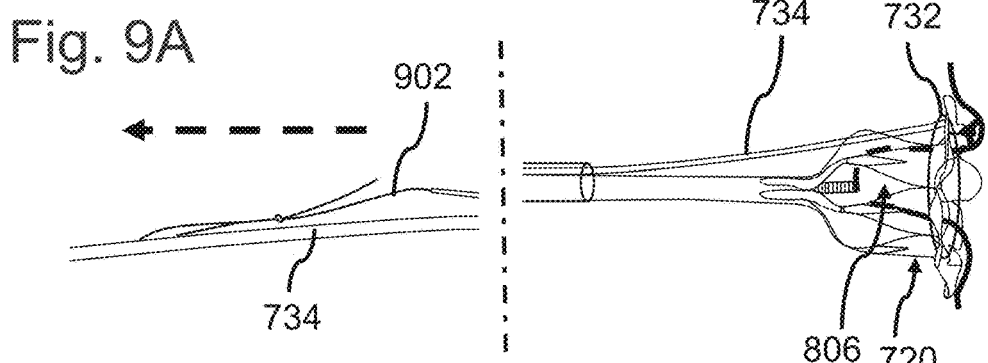
Figure 9B:
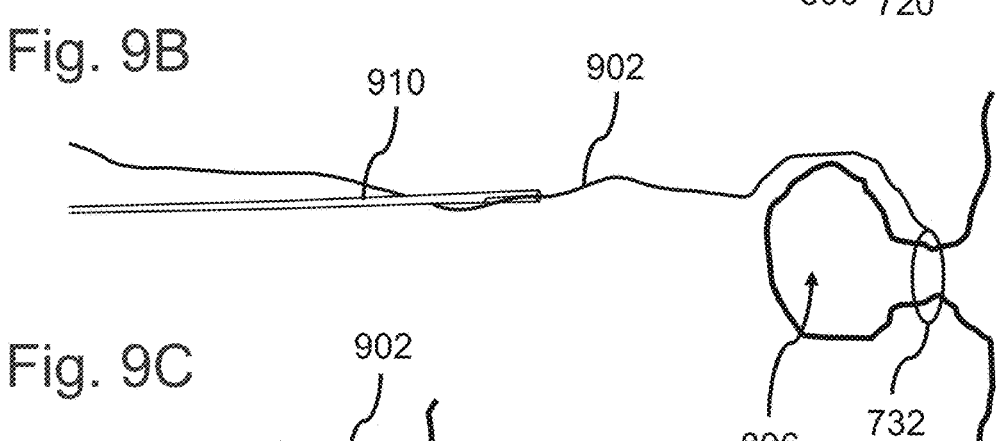
Figure 9C:
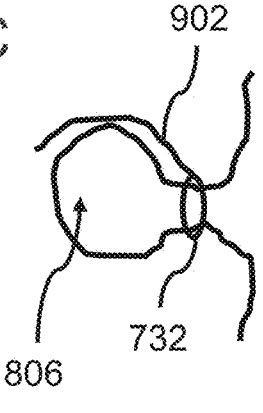

Reference is now made to FIGS. 9A-9C, depicting invaginated LAA closure by at least one ligator, according to some exemplary embodiments of the invention.

According to some exemplary embodiments, for example as shown in FIG. 9A, once the LAA 806 is invaginated into the cup 720, the ligator loop 732 is tightened around the invaginated LAA, for example around a base of the invaginated LAA. In some embodiments, the loop 732 is tightened, for example irreversibly tightened, by retracting a wire 902 located within the shaft 734, for example the sleeve. In some embodiments, tightening of the loop 732 decouples the loop 732 from the cup 720.

According to some exemplary embodiments, once the loop 732 is tightened around the invaginated LAA, the LAA isolator is retracted from the LA into and via the working channel. Optionally or additionally, the sleeve 734 is retracted from the loop 732, leaving a suture 902 connected to the loop 732.

According to some exemplary embodiments, for example as shown in FIG. 9B, a cutter, for example suture cutter 910 is advanced within the LA towards the loop 732, for example towards the tightened loop. In some embodiments, the suture cutter 910 advances within the working channel, and optionally over suture 902 towards the loop 732. In some embodiments, for example as shown in FIG. 9C, the suture cutter 902 cuts the suture 902 close to the loop 732, for example at a distance shorter than 3 cm, for example shorter than 2 cm, shorter than 1 cm, shorter than 0.5 cm, shorter than 0.2 cm or any intermediate, shorter or longer distance from the loop 732.

According to some exemplary embodiments, for example as shown in FIG. 9C, following the cutting of the suture 902, the suture cutter 910 is retracted from the LA and from the heart into and via the working channel. In some embodiments, when the LAA closure is completed, the guide instrument is retracted from the LA, and from the heart, leaving the invaginated LAA 806 closed by the ligator loop 732 within the LA.

Exemplary Ligator

Reference is now made to FIGS. 10A-10C ligators, for example ligation devices, according to some exemplary embodiments of the invention.

According to some exemplary embodiments, for example as shown in FIGS. 10A and 10B, a ligator 1002 comprises a lasso 1004 passing through a cinch 1006 which divides the lasso into two portions, a first portion 1008 and a second portion 1010. In some embodiments, the ligator 1002 comprises a delivery tube 1012, in which the lasso 1004 passes until reaching the LA or the LAA. In some embodiments, the ligator comprises a rod 1014 terminating with a grasper, for example a hook 1016, configured to grasp a second proximal section 1010 of the lasso 1008 and to pull the second proximal portion 1010 towards the tube 1012. In some embodiments, for example as shown in FIG. 10B, pulling the second proximal portion 1010 towards, for example into the tube 1012, tightens the first distal portion 1008, for example around an inverted or an invaginated tissue, for example the LAA.

According to some exemplary embodiments, the tube 1012 is a flexible tube, for example flexible in a lateral direction, for example to allow passing of the tube within a catheter. In some embodiments, the tube 1012 is bendable, for example to allow bending of the tube 1012 while passing within a catheter.

According to some exemplary embodiments, for example as shown in FIG. 10C, a ligator comprises a rubber band 1018, and a rubber band placement mechanism. In some embodiments, the rubber band 1018 is positioned around the tube 1022, and is configured to be moved by the rubber band placement mechanism onto an invaginated portion 1024 of the LAA. Optionally the invaginated portion 1024 is held by the tube 1022, for example a vacuum tube.

According to some exemplary embodiments, the rubber band placement mechanism comprises a rod 1026 coupled o the rubber band 1018. In some embodiments, the rod 1026 is a rigid rod, for example in an axial direction, and is configured to move the rubber band 1018 along an external surface of the tube 1022 and/or onto the invaginated portion 1024.

Exemplary Grasper Retrieval

According to some exemplary embodiments, a ligator is reversibly tightened around a tissue, for example an invaginated LAA. Reference is now made to FIGS. 10D and 10E, depicting a ligator retrieval device, according to some exemplary embodiments of the invention.

According to some exemplary embodiments, while the lasso 1004 is tightened around a tissue, the hook 1016 is attached to a second proximal section 1010 of the lasso 1004. In some embodiments, for example as shown in FIG. 10E, a cinch grasper 1026 is attached to the cinch 1006 and pulls the cinch 1006 towards the tube 1012. In some embodiments, pulling the cinch towards the tube 1012 untightens the second distal portion 1008 allowing removal of the lasso 1004 from the tissue.

Exemplary Suction Channel Distal End

According to some exemplary embodiments, a distal end of a suction channel is shaped and sized to be placed in contact with the LAA wall, and to invert a portion of the LAA wall into the suction channel lumen. Reference is no made to FIGS. 11A-11C depicting different types of suction channel distal ends configured to hold an inverted LAA wall within the suction channel, according to some exemplary embodiments of the invention.

According to some exemplary embodiments, for example as shown in FIG. 11A, a suction channel distal end 1102 comprises inwardly facing hooks or an inwardly bended edge 1104, bended into a lumen 1106 of the suction channel. In some embodiments, the inwardly bended edge 1104 surrounds a distal opening of the channel through which the inverted LLA wall 1110 penetrates into the suction channel.

According to some exemplary embodiments, for example as shown in FIG. 11B, an inner surface of the suction channel distal end 1113, comprises a plurality of teeth 1114 or short protrusions, configured to contact and at least partly hold the inverted LLA wall 1110. In some embodiments, the plurality of teeth 1114 or short protrusions surround the distal opening 1108 through which the inverted LLA penetrates into the suction channel.

According to some exemplary embodiments, for example as shown in FIG. 11C, an inner surface of the suction channel distal end 1118 is a non-smooth rough surface 1120, configured to increase contact area with the inverted LLA wall. In some embodiments, the non-smooth rough surface is a coating. In some embodiments, the non-smooth rough surface surrounds the distal opening 1108 of the suction channel.

According to some exemplary embodiments, an edge of the suction channel placed in contact with the LAA wall is rounded, for example to prevent damage to the LAA wall.

According to some exemplary embodiments, for example as shown in FIG. 11D, a suction channel 1130 extends from a working channel 1131 of a tube 1132, for example a guiding tube 1132 within the LAA 1134. In some embodiments, the guiding tube 1132 has an inner diameter or width in a range of about 1 mm to about 25 mm, for example about 2 mm to about 10 mm, about 5 mm to about 20 mm, about 10 mm to about 20 mm, about 15 mm to about 25 mm or any intermediate, smaller or larger range of values. In some embodiments, the guiding tube 1132 has an outer diameter or width in a range of about 1 mm to about 25 mm, for example about 2 mm to about 10 mm, about 5 mm to about 20 mm, about 10 mm to about 20 mm, about 15 mm to about 25 mm or any intermediate, smaller or larger range of values. In some embodiments, the suction channel 1130 has an inner diameter or width in a range of about 1 mm to about 25 mm, for example about 2 mm to about 10 mm, about 5 mm to about 20 mm, about 10 mm to about 20 mm, about 15 mm to about 25 mm or any intermediate, smaller or larger range of values. In some embodiments, the suction channel 1130 has an outer diameter or width in a range of about 1 mm to about 25 mm, for example about 2 mm to about 10 mm, about 5 mm to about 20 mm, about 10 mm to about 20 mm, about 15 mm to about 25 mm or any intermediate, smaller or larger range of values.

According to some exemplary embodiments, for example as shown in FIG. 11D, the suction channel 1130 terminates with an outwardly expanding suction head 1136. In some embodiments, the suction head 1136 is an expandable suction head. In some embodiments, the suction head 1136 is flexible and/or soft, for example not to damage a wall of the LAA. In some embodiments, application of vacuum through the suction channel 1130, inverts a portion of the LAA wall 1138 into the suction head 1136, for example through a distal opening 1140 of the suction head 1136. In some embodiments, the suction head is optionally tapered. In some embodiments, the suction head is optionally concave.

Exemplary Suction Tube

According to some exemplary embodiments, for example as shown in FIG. 12, a catheter 1204 is navigated into the LA. In some embodiments, a tube, for example a suction tube 1202 of an LAA invaginator is configured to be introduced into the LAA 1206. In some embodiments, the suction tube 1202 is a steerable suction tube, configured to controllably bend within the LAA, for example according to LAA anatomy. In some embodiments, the suction tube 1202 controllably bends within the LAA according to the shape and size of the inner lumen of the LAA, for example to reach a target region within the LAA. In some embodiments, the suction tube 1202, for example a distal end 1208 of the suction tube 1202 is at least partly radiopaque, for example to allow visualization of the suction tube 1202 within the LAA.

Exemplary Suction Feedback

Figure 13:
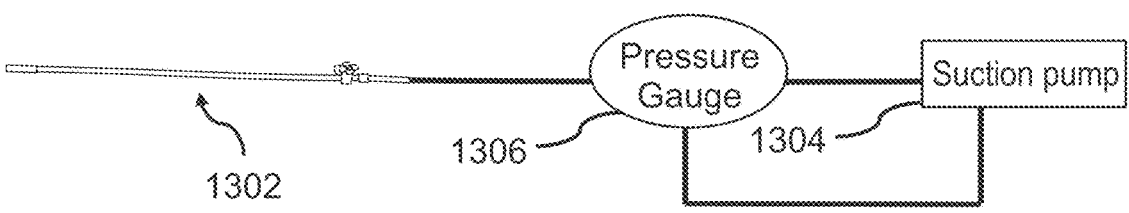
FIG. 13 is a schematic illustration of a pressure feedback loop, according to some exemplary embodiments of the invention.

According to some exemplary embodiments, for example as shown in FIG. 13, the suction channel 1302 is fluidically connected to a suction pump 1304, for example a vacuum pump or syringe via a pressure gauge 1306. In some embodiments, if the pressure within the suction channel is lower than a predetermined value, for example 760 mmHg, then the suction pump automatically stops application of vacuum.

Exemplary Collapsible Tissue Grasper

Figure 14C:
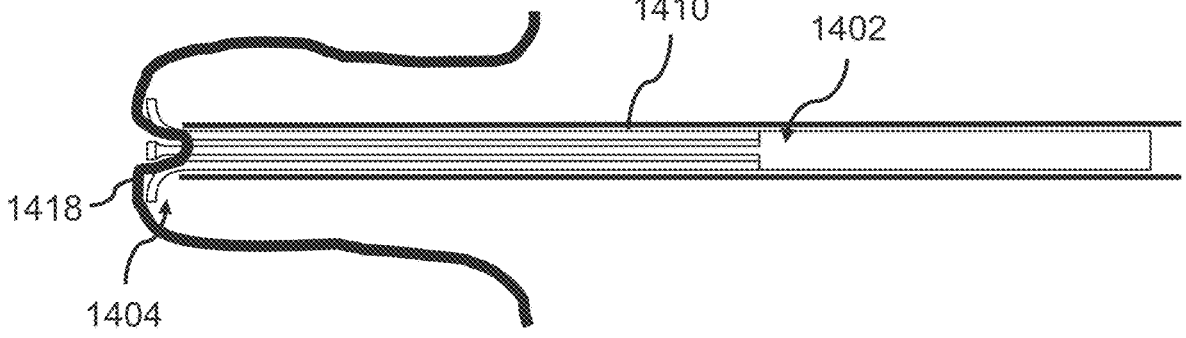

Reference is now made to FIGS. 14A-14C, depicting a tissue grasper comprises clamps, according to some exemplary embodiments of the invention.

According to some exemplary embodiments, a tissue grasper, for example tissue grasper 1402, comprises one or more extensions, for example clamps 1404. In some embodiments, a distal end 1406 of each clamp 1404 is bended outwardly in at least 80 degrees, for example at least 90 degrees, at least 100 degrees or any intermediate, smaller or larger angle relative to a longitudinal axis 1408 of the grasper 1402.

According to some exemplary embodiments, for example as shown in FIGS. 14B and 14C, the clamps 1404 extend out from a working channel 1410, for example a suction channel, within the LAA 1412. In some embodiments, the clamps 1404, for example a distal end of each clamp, are placed in contact with the LAA wall 1414. Add applying vacuum to invaginate small LAA tissue into the clamps that are covered by a polyurethane or other. In some embodiments, retraction of the grasper into the working channel 1410 collapses the clamps 1404 while grasping an inverted portion of the LAA wall 1418 therebetween. In some embodiments, when collapsed, the clamps 1404 pinch an inverted portion of the LAA wall 1418. In some embodiments, retraction of the grasper and/or the working channel 1410 while the LAA wall is pinched or grasped by the clamps 1404, invaginates the LAA, for example into the LA.

According to some exemplary embodiments, for example as shown in FIG. 14C, the in a closed state, for example when the clamps are pressed against the inverted LAA wall portion 1418 they apply a force in a range of about 3 Newton (N) to about 35 N, for example about 5 N to about 15 N, about 10 N to about 20 N, about 15 N to about 25 N, about 20 N to about 30 N or any intermediate, smaller or larger range of values, on the inverted LAA portion. In some embodiments, the fore applied by the clamps is sufficient to grasp the inverted LAA portion, for example during invagination of the LAA into the LA.

Reference is now made to FIGS. 15A-15D depicting a collapsible tissue grasper, according to some exemplary embodiments of the invention.

Figures 15A, 15B, 15C, 15D:
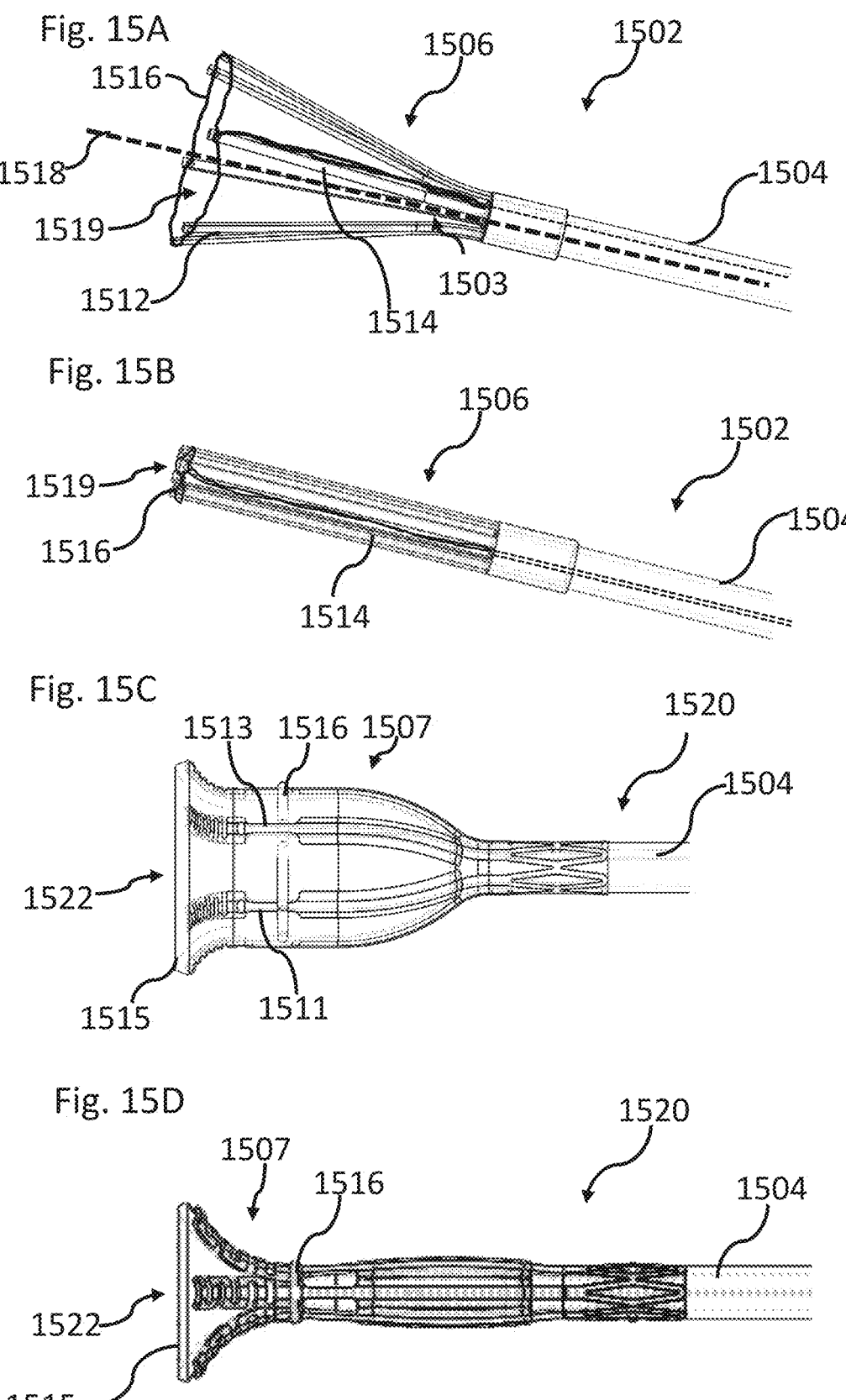
FIGS. 15A and 15B are schematic illustrations of a collapsible tissue grasper having a plurality of extensions, according to some exemplary embodiments.
FIGS. 15C and 15D are schematic illustrations of a collapsible tissue grasper having a collapsible cup, according to some exemplary embodiments of the invention.

According to some exemplary embodiments, for example as shown in FIGS. 15A and 15B, a tissue gasper comprises an elongated portion 1504 terminating with a collapsible distal end 1506. In some embodiments, the collapsible distal end 1506 is configured to move between an open state and a closed state, for example by moving a grasper manipulator coupled to the collapsible distal end 1506. In some embodiments, the grasper manipulator comprises a rod, and/or a wire coupled to the collapsible distal end 1506.

According to some exemplary embodiments, the elongated portion 1504 comprises a tube, optionally forming a channel 1504, coupled to the collapsible distal end 1506. Alternatively, the elongated portion comprises an elongated rod coupled to the collapsible distal end 1506.

According to some exemplary embodiments, the collapsible distal end 1506, comprises a plurality of elongated supporting extensions shaped as fingers, for example fingers 1512 and 1514. In some embodiments, a proximal end of each of the fingers is coupled, for example movably coupled to the elongated portion 1504, and is arranged to surround a distal opening 1503 of the elongated portion 1504. Optionally each of the fingers is coupled to the elongated portion by a hinge, for example a hinge between the proximal end of each of the fingers and the elongated portion 1504. In some embodiments, the fingers are interconnected to each other, for example by at least one wire 1516 coupled to a distal end of the fingers. In some embodiments, the wire 1516 forms a loop, for example a lasso coupled to each finger or to at least some of the fingers.

According to some exemplary embodiments, when the collapsible distal end 1506 is in an expanded, open, state, each of the fingers is tilted, for example outwardly tilted, relative to an elongated axis 1518 of the tissue grasper 1502. In some embodiments, tilting of the fingers opens the lasso, formed by the wire 1516. Additionally, or alternatively, tilting of the fingers relative to the longitudinal axis of the device 1502, opens a distal opening 1519 of the collapsible distal end 1506, for example to receive a portion of an inverted LAA into the distal collapsible cup 1506.

According to some exemplary embodiments, the collapsible distal end 1506 is configured to collapse, for example by moving the grasper manipulator, optionally from outside the body. In some embodiments, the collapsible distal end 1506 is configured to reversibly collapse. In some embodiments, in a collapsed state, the collapsible distal end 1506, and the distal opening 1519 is at least partly closed, for example to grasp the invaginated portion of the LAA, positioned within an inner lumen of the collapsible distal end 1506.

According to some exemplary embodiments, for example as shown in FIGS. 15C and 15D, a collapsible grasper 1520 comprises an elongated portion 1502, for example a vacuum channel, and a distal collapsible cup 1507 at a distal end of the vacuum channel.

According to some exemplary embodiments, the distal collapsible cup 1507 comprises a sheet material coupled to 3 or more extensions, for example fingers 1511 and 1513. In some embodiments, a proximal end of each extension is coupled to a distal end of the tube 1504, or are positioned within the tube, for example as shown in FIGS. 15C and 15D. Optionally, a distal section of each of the fingers is outwardly curved, for example to form a collapsible cup with a wide distal opening 1522, where a distal edge 1515 of the cup is shaped and sized to contact the LAA without causing injury to the LAA wall. In some embodiments, the edge 1515 is soft and/or flexible. Alternatively or additionally, the edge is outwardly curved in an angle smaller than 45 degrees, for example smaller than 30 degrees, smaller than 20 degrees, smaller than 10 degrees, or any intermediate, smaller or larger angle relative to a cross section of the distal opening 1522. Optionally, and outwardly curved edge of the distal cup allows to contact the LAA wall with reduced force.

According to some exemplary embodiments, collapsible cup 1507 is shaped and sized to apply vacuum from said vacuum channel through said distal opening 1522 on a tissue, for example a LAA wall. In some embodiments, the collapsible cup 1507 is configured to move between an open state, for example when the fingers are tilted outwardly to stretch the sheet layer and expand the distal opening 1522, for example as shown in FIG. 15C, and a closed state, for example as shown in FIG. 15D, where the collapsible cup 1507 is collapsed and the distal opening 1522 is closed.

According to some exemplary embodiments, the collapsible grasper, is configured to be expanded in a relaxed state and to reversibly collapse when a force is applied, for example on one or more of the fingers. Alternatively, the collapsible grasper is configured reversibly collapse when a force is applied on a wire 1516 forming the lasso.

According to some exemplary embodiments, in order to grasp an invaginated portion of the LAA, the grasper 1502 is introduced through the LAA opening into the LAA. Optionally, the grasper 1502 is introduced in a collapsed state into the LAA. In some embodiments, the collapsible distal end 1502 expands within the LAA, and is advanced towards the LAA wall, to place an invaginated portion of the LAA wall within the distal opening 1519. In some embodiments, when the invaginated portion of the LAA wall is within the distal opening 1519, a force is applied on the wire to close the lasso on the invaginated portion of the LAA wall. In some embodiments, closing, for example tightening the lasso, reversibly collapses the collapsible distal end 1506 of the invaginated portion of the LAA wall with a force that is sufficient to hold the invaginated portion of the LAA wall within the collapsible distal end 1506, while retracting the grasper 1502 into the LA.

According to some exemplary embodiments, in order to grasp a portion of the LAA wall, the distal collapsible cup 1507 is introduced into the IAA, for example in a collapsed state. In some embodiments, the collapsible cup is optionally expanded within the IAA and is placed in contact with the LAA wall. In some embodiments, vacuum is applied from a vacuum channel connected to the cup, for example vacuum channel 1504, via the distal opening 1522 on the LAA wall. In some embodiments, the vacuum is applied with a force sufficient to invaginate a portion of the LAA wall into a lumen of the cup 1507 through the distal opening 1522. In some embodiments, the distal collapsible cup 1507 is collapsed on the invaginated portion of the LAA with a force sufficient to grasp the invaginated portion. Optionally, the distal collapsible cup 1507 is collapsed on the invaginated portion of the LAA wall, while vacuum is applied on the LAA wall, for example to keep the invaginated portion of the LAA wall within the lumen of the cup 1507. In some embodiments, applying force on a wire or a ring forming a lasso, for example wire 1516, closes the lasso, for example as shown in FIG. 15D. In some embodiments, closing the lasso, reversibly collapses the collapsible cup 1507 on an invaginated portion of the LAA wall.

According to some exemplary embodiments, the collapsible grasper is shaped and sized to be positioned and move within a catheter, for example within a working channel of a catheter introduced into the heart, optionally when the distal collapsible cup is in a collapsed state. Optionally, the collapsible grasper is shaped and sized to be positioned and move within an elongated tube of an LAA isolator, optionally when the distal collapsible cup is in a collapsed state.

According to some exemplary embodiments, the collapsible grasper is retracted into the LA while the cup is collapsed over the invaginated LAA wall portion, for example to invaginate the LAA into the LA. Optionally, the collapsible grasper is retracted through a distal opening of a ligator, for example to position the ligator around the invaginated LAA. Optionally, the collapsible grasper is retracted into the LA through at least one loop, ring, lasso, clip of the ligator.

Exemplary Grasper Cup with Ring Holders

According to some exemplary embodiments, a cup of a tissue grasper has a leading edge that is configured to be placed in contact with the LAA wall. In some embodiments, the contact between the tissue grasper cup edge and the LAA is sufficiently close to allow application of vacuum via the cup on the LAA wall without or with minimal leakage through an interface between the cup and the LAA wall. In some embodiments, the cup leading edge is covered with a smooth layer, for example a smooth layer of fabric, that allows to form, for example, a sealed interface between the cup leading edge and the LAA wall.

According to some exemplary embodiments, the smooth layer comprises a plurality of ring holders surrounding the cup opening. In some embodiments, each of the ring holders comprises a channel which is shaped and sized to receive a wire of a cup closure device. In some embodiments, the wire surrounds the cup opening, and allows, for example, collapse of the cup when the wire is retracted and expansion of the cup when the wire is in a relaxed state.

Reference is now made to FIGS. 16A-16F depicting a tissue grasper cup having a smooth leading edge cover, according to some exemplary embodiments of the invention.

Figures 16A, 16B, 16C:
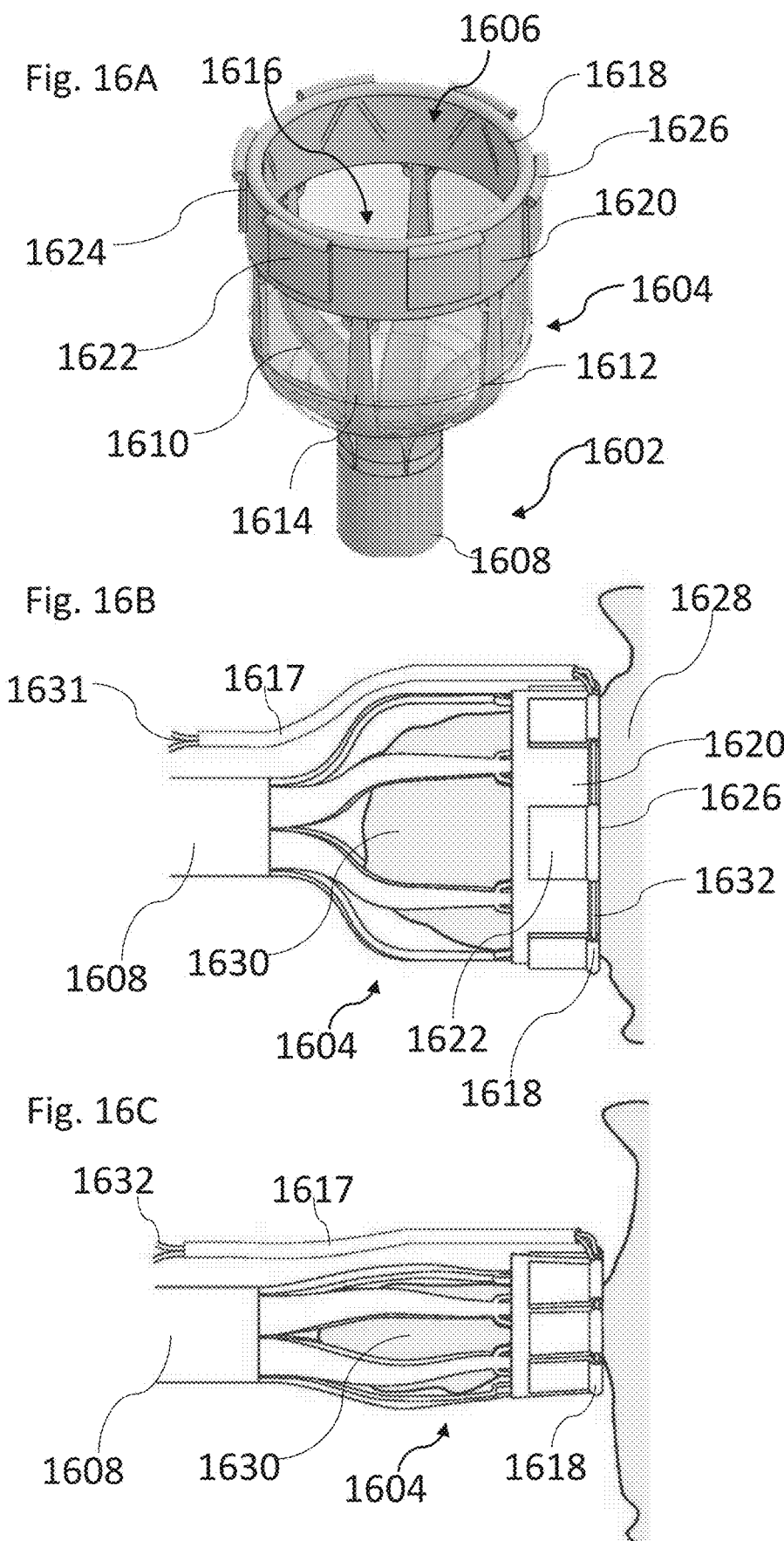
FIGS. 16A-16F are schematic illustrations of a tissue grasper collapsible cup comprising a plurality of ring holders coupled to a wall of the collapsible cup, according to some exemplary embodiments of the invention.

According to some exemplary embodiments, for example as shown in FIGS. 16A and 16B, a tissue grasper 1602 comprises a cup 1604, for example a collapsible cup, having a distal opening 1606. In some embodiments, the cup 1604 is coupled to an elongated body 1608, for example an elongated tube or an elongated shaft. In some embodiments, the elongated body 1608 of the tissue grasper terminates with the cup 1604. In some embodiments, the elongated body 1608 is a suction tube coupled to a vacuum source, for example a vacuum pump or a syringe.

According to some exemplary embodiments, the cup, for example cup 1604 is configured to move between a collapsed state, for example when the tissue grasper is navigated to the heart within a catheter having a narrow lumen, and an expanded state within the LAA prior to contacting LAA wall. In some embodiments, the cup is covered with a sheet material 1610. In some embodiments, the cup 1604 comprises a plurality of movable extensions, for example fingers 1612 and 1614 surrounding an inner lumen 1616 of the cup 1604. In some embodiments, the sheet material 1610 is coupled to the plurality of movable extensions. In some embodiments, the fingers 1612 and 1614 are similar to extensions, for example fingers 1511 and 1513 shown in FIGS. 15C and 15D.

According to some exemplary embodiments, the tissue grasper comprises a ring, for example ring 1632, coupled to the cup 1604, for example to the cup wall. In some embodiments, the ring surrounds the cup 1604, for example the ring surrounds the distal opening 1606 of the cup 1604. In some embodiments, the ring 1632 is formed from at least one wire. In some embodiments, tightening of the ring 1632, for example by moving of at least one wire coupled to the ring 1632, or moving of at least one wire forming the ring 1632, tightens the ring and moves the cup 1604 to a collapsed state, for example as shown in FIG. 16C.

According to some exemplary embodiments, a leading edge 1618 of the cup 1604, which is configured to be placed in contact with a wall of the LAA, is covered with a layer 1620 of smooth material, for example fabric, that is configured to contact the LAA without causing damage to the tissue of the LAA wall, and to form a sealed attachment to the LAA wall to allow, for example efficient application of vacuum on the LAA wall from within the cup. In some embodiments, the leading edge 1618 of the cup 1604 surrounds the cup opening 1606.

According to some exemplary embodiments, the layer 1620 of smooth material is coupled to the sheet material 1610 of the cup. Alternatively, the layer 1620 is integrally formed with the sheet material 1610.

According to some exemplary embodiments, the layer 1620 comprises a plurality of ring holders coupled to the layer 1620 and surrounding the opening 1606, for example ring holders 1620 and 1624. In some embodiments, each of the ring holders is shaped as a patch coupled to the layer 1620.

According to some exemplary embodiments, each of the ring holders comprises a channel 1626 adjacent to the leading edge 1618 of the cup 1604, and is shape and sized to hold the ring 1632, for example to receive a wire, for example a suture wire, forming the ring 1632. In some embodiments, when the wire travels within the channels of each wore holder, the wire surrounds the cup 1604 and optionally the distal opening 1606.

According to some exemplary embodiments, for example as shown in FIGS. 16A and 16B, the patches of ring holders are spaced-apart from each other. In some embodiments, the wire holder patches are formed from a same material as layer 1610 or from any other fabric.

According to some exemplary embodiments, for example as shown in FIG. 16B, the cup 1604 is placed in contact with the LAA wall 1628. In some embodiments, the smooth layer 1620 covering the leading edge 1618 is placed in contact with the LAA wall 1628. In some embodiments, application of vacuum onto the LAA wall 1628 through the cup 1604 and opening 1606 inverts a portion 1630 of the LAA wall 1628 into the cup 1604.

According to some exemplary embodiments, for example as shown in FIG. 16C, retraction of at least one wire 1631 coupled to the ring 1632 or forming the ring 1632 collapses the leading edge 1618 on a base of the LAA wall portion 1630 located within the cup 1604, with a force that is sufficient to hold the LAA wall portion 1630 within the cup 1604 when the tissue grasper is retracted into the LA, for example as shown in FIG. 6E. In some embodiments, retraction of the wire 1631 collapses, for example reversibly collapses, the cup 1604 on the tissue 1630.

According to some exemplary embodiments, for example as shown in FIGS. 16A-16C, the ring holders are attached to an external surface of the cup 1604 for example to layer 1620. In some embodiments, the ring holders are attached to the external surface of the cup 1604 in an orientation that aligns a channel 1626 of each wire holder through which the wire 1632 passes, with the leading edge 1618 of the cup 1604.

According to some exemplary embodiments, the at least one tissue grasper 1602 comprises a tube or a shaft 1617, for example a flexible and/or a bendable shaft. In some embodiments, the shaft 1617 is coupled, for example mechanically connected, to the ring 1632. In some embodiments, rotation, twisting and/or maneuvering of the shaft 1617, tightens and/or loosens the ring 1632. Optionally, maneuvering of the shaft 1617, locks the ring 1632 at a tightened state and/or at a loose state. Optionally, maneuvering of the shaft 1617 allows, for example, to disconnect the shaft 1617 from the ring 1632, for example when the ring 1632 is at a tightened state. Alternatively, the shaft 1617 is hollow, and a wire connected to the ring 1632 travels within the inner lumen of the shaft 1617.

Figures 16D, 16E, 16F:
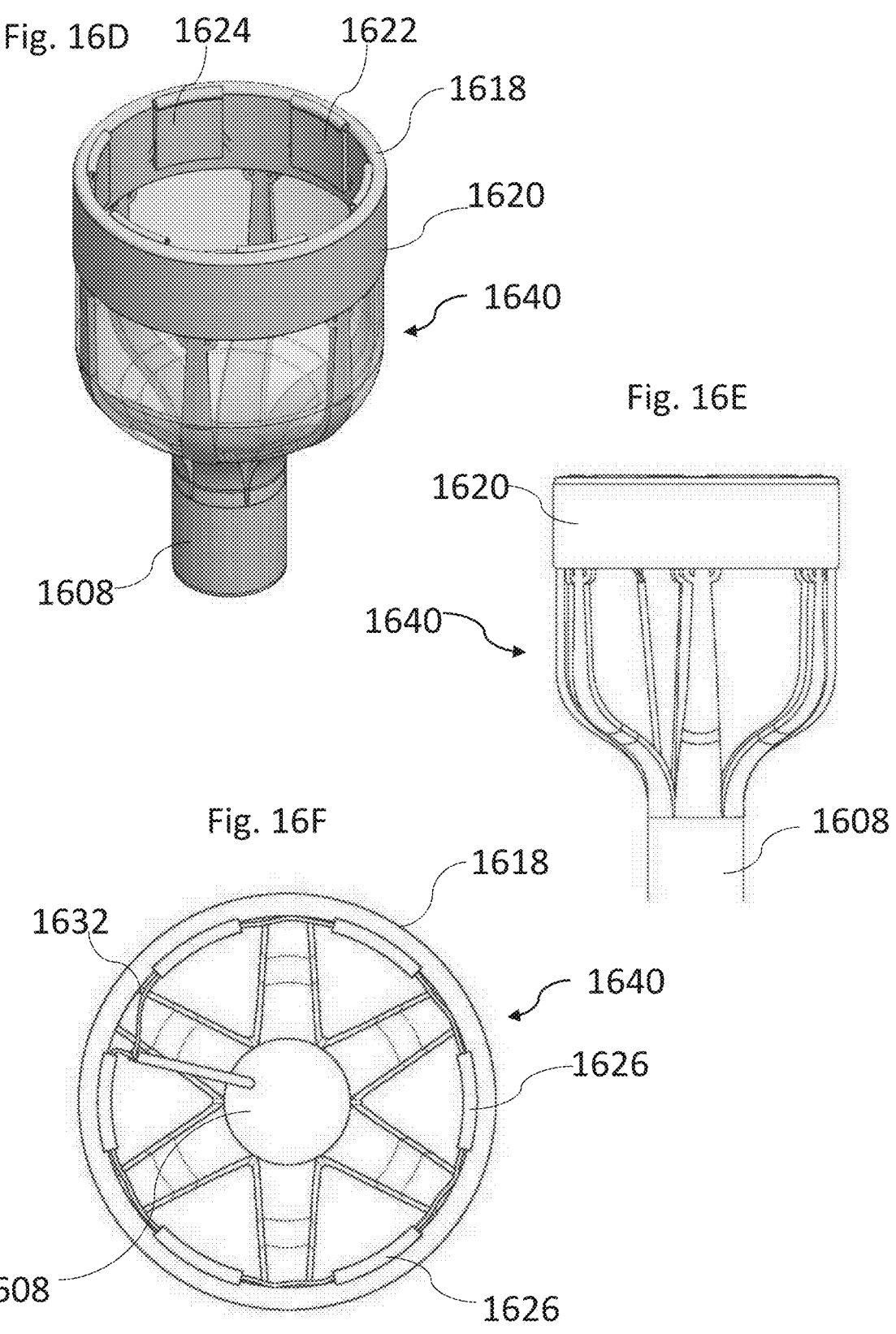

According to some exemplary embodiments, for example as shown in FIGS. 16D-16F, the ring holders 1622 and 1624 are coupled to the inner surface of the cup 1640, optionally in an orientation that aligns a channel 1626 of each wire holder through which the wire 1632 passes with the leading edge 1618 of the cup 1640.

Exemplary Grasper Cup with Extendable Capturing Ring

According to some exemplary embodiments, the tissue grasper cup comprises a ring configured to be positioned around and to be tightened, for example reversibly tightened around a portion of the LAA wall positioned inside the cup. In some embodiments, for example as shown in FIGS. 16A-16F, the capturing ring is held around the distal opening of the cup by a plurality of ring holders. Alternatively, the plurality of ring holders are extendable, for example to allow advancement of the ring distally to the cup opening. A potential advantage of advancing the ring distally to the grasper cup may be to allow tightening of the ring around a base of a larger portion of the LAA wall grasped by the tissue grasper cup.

Grasping of a large portion of the LAA prior to and during the retraction of the LAA wall into the LA may allow stable retraction and prevent release of the LAA wall from the tissue grasper during the inversion process.

Reference is now made to FIGS. 17A-17E, depicting a tissue grasper cup with an extendable capturing ring, according to some exemplary embodiments of the invention.

According to some exemplary embodiments, a tissue grasper 1700 comprises a cup 1702 defining an inner lumen having a distal opening 1702. In some embodiments, the cup comprises a leading edge 1706 surrounding the distal opening 1702. In some embodiments, the leading edge 1706 of the cup is configured to be placed in contact with the wall of the LAA, and to allow application of vacuum via the tissue grasper and the cup 1702 on the LAA wall. In some embodiments, the vacuum applied is sufficient to convex a portion of the LAA wall into the cup 1702.

According to some exemplary embodiments, for example as also discussed in FIGS. 16A-16F, the tissue grasper comprises a capturing ring 1708 associated with the cup 1702. In some embodiments, the capturing ring 1708 is formed from a wire 1718, for example a suture, coupled to the cup 1702 by a plurality of ring holders, for example ring holders 1710, 1712, and 1714 surrounding the cup 1702. In some embodiments, each of the ring holders comprises a channel, for example channel 1716, configured to receive and hold the ring 1708. In some embodiments, for example as shown in FIGS. 16A-16F, a position of the ring holders relative to the cup distal end is fixed, and the ring is optionally surrounding the leading edge of the 1706 or is located within the cup next to the leading edge. Alternatively, for example as shown in FIGS. 17A-17E, the ring holders of cup 1702 are extendable, and are configured to extend the ring 1708 distally to the leading edge 1706 of the cup 1702.

According to some exemplary embodiments, the extendable ring holders 1710, 1712 and 1714, optionally formed as patches, are coupled to an external surface of the cup and/or to an internal surface of the cup. In some embodiments, the extendable ring holders are coupled to a material layer 1716 surrounding the distal end of the cup 1702 and/or the leading edge 1706 of the cup 1702. Alternatively, the extendable ring holders are coupled directly to the cup body, for example to a layer or a membrane surrounding the inner lumen of the cup.

According to some exemplary embodiments, the ring holders are configured to extend, for example by moving, optionally gradually moving, from a folded state, in which the ring is held adjacent to the leading edge or proximal to the leading edge, to an unfolded state, in which the ring is extended distally to the leading edge. Alternatively, the ring holders are configured to flip between a reverse or a backward state to a forward state.

According to some exemplary embodiments, the at least one tissue grasper 1700 comprises a tube or a shaft 1617, for example a flexible and/or a bendable shaft. In some embodiments, the shaft 1617 is coupled, for example mechanically connected, to the ring 1708. In some embodiments, rotation, twisting and/or maneuvering of the shaft 1617, tightens and/or loosens the ring 1708. Optionally, maneuvering of the shaft 1617, locks the ring 1708 at a tightened state and/or at a loose state. Optionally, maneuvering of the shaft 1617 allows, for example, to disconnect the shaft 1617 from the ring 1708, for example when the ring 1708 is at a tightened state. Optionally, the shaft 1617 is hollow, and a wire 1718 connected to the ring 1708 travels within the inner lumen of the shaft 1617. In some embodiments, maneuvering, for example advancing or retracting the wire 1718 loosens or tightens the ring 1708.

According to some exemplary embodiments, maneuvering of the shaft 1617, for example forwardly moving the shaft 1617 towards a LAA wall, advances the ring 1708 distally to the leading edge 1706, and moves the ring holders from a folded state to an extended, unfolded, state.

Reference is now made to FIGS. 17C-17E, depicting a tissue grasping process using a tissue grasper with an extendable capturing ring, according to some exemplary embodiments of the invention.

According to some exemplary embodiments, for example as shown in FIG. 17C, a cup 1702, for example a suction cup of a tissue grasper coupled to a distal end of tube 1703, for example suction tube, is placed in contact with LAA wall 1718. In some embodiments, the tube 1703 is similar to the elongated body 1608 shown in FIGS. 16A-16F. In some embodiments, a leading edge 1706 of the cup 1702 is placed in contact with the LAA wall 1718. In some embodiments, vacuum is applied via the suction tube 1703 and the distal opening of the cup 1702 on the LAA wall 1718 with force that is sufficient to convex a portion 1720 of the LAA wall 1718 into the inner lumen of the cup 1702 via the cup distal opening. In some embodiments, for example as shown in FIG. 17C, when the leading edge 1706 contact the LAA wall 1718 to allow convexing of the LAA wall portion using vacuum, the ring holders, for example ring holders 1710, 1712 and 1714 are in a non-extendable state, for example a folded state or a backward state.

According to some exemplary embodiments, for example as shown in FIG. 17D, following the convexing, for example partial invagination, of the LAA wall into the grasper cup 1702 in FIG. 17C, the ring holders are forwardly extended, at least partially distally to the leading edge 1706. In some embodiments, the ring holders are forwardly extended by maneuvering the shaft 1617 coupled to the ring 1708, for example by forwardly advancing the shaft 1617 towards the LAA wall 1718. In some embodiments, a ring 1722, for example a tissue capturing ring, coupled to the ring holders and/or to the shaft 1617, is moved distally to the leading edge 1706. In some embodiments, the ring 1708 moves distally relative to the leading edge 1706 by the movement of the ring holders, for example ring holders 1410, 1412 and 1414 to an extended state.

According to some exemplary embodiments, the ring holders, for example as shown in FIG. 17D, move to an unfolded state, for example by advancement of the shaft 1617, functioning as a guide for a wire 1705 optionally forming the ring 1708. In some embodiments, at least one wire 1705 forming the ring 1708 passes within the shaft 1617. In some embodiments, the shaft 1617 and the wire 1705 forming the ring 1708 are part of the tissue grasper device, or the tissue grasper assembly. Optionally, the shaft 1617 is coupled to the suction tube 1703 and passes within the suction tube 1703 or outside the suction tube, 1703 from the suction cup 1702 of the grasper to a location outside the body, for example to allow manipulation of the tissue grasper from outside the body.

According to some exemplary embodiments, in case where the ring holders are flipping ring holders, forwardly advancement of the shaft 1617 flips the ring holders from a backward state to a forward state. In some embodiments, retraction of the shaft 1617 flips the ring holders to a backward state, or moves the ring holders from an unfolded state to a folded state.

According to some exemplary embodiments, for example as shown in FIG. 17E, following advancement of the ring 1708 distally to the leading edge 1706 of the cup 1702, the ring 1708 is tightened around a base of the LAA wall portion 1720 located within the cup 1702. In some embodiments, the ring 1708 is tightened by manipulating the wire 1705 and/or the shaft 1617, for example by retracting, twisting or forwardly moving the wire 1705 or shaft 1617. In some embodiments, the tissue grasper is retracted into the LA while the ring is tightened, to invaginate the LAA, at least partly into the LA, for example as described at block 420 in FIG. 4. In some embodiments, the ring 1708 formed from a wire is tightened around the LAA tissue with a force that is lower than a force needs to puncture or cut the LAA tissue. In some embodiments, the ring 1708 is tightened with a force in a range between 15 Newtons (N) and 50 N, for example with a force in a range between 20 N and 40 N, with a force in a range between 25 N and 35 N, or any intermediate, smaller or larger range of forces.

It is expected that during the life of a patent maturing from this application many relevant ligation devices will be developed; the scope of the term LAA ligator is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein, and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for left atrial appendage (LAA) invagination, comprising:

convexing a portion of the LAA wall into the LAA, wherein said convexing comprises convexing said LAA wall portion by applying suction from a collapsible suction cup contacting said LAA wall on said LAA wall portion;

grasping said convexed LAA wall portion within the LAA, following said convexing;

invaginating said LAA at least partly into the left atria (LA) using said convexed LAA portion;

wherein said grasping comprises controllably collapsing said collapsible suction cup on said convexed LAA portion with a force sufficient to hold said convexed LAA portion during said invaginating.

2. A method according to claim 1, wherein said convexing comprises convexing said LAA wall portion to a distance of up to 2 cm into the LAA.

3. A method according to claim 1, wherein said convexing comprises applying force on an inner surface of said LAA wall from within the LAA, which is sufficient to convex said LAA wall portion into the LAA.

4. A method according to claim 3, wherein said applied force is atraumatic to the LAA wall.

5. A method according to claim 1, wherein said convexing and said grasping are separated in time.

6. A method according to claim 1, wherein said convexing comprises applying a first force on a region of said LAA wall which is sufficient to convex said LAA wall portion, and wherein said grasping comprises applying a second force on a smaller portion of said region to grasp said convexed LAA wall portion.

7. A method according to claim 1, wherein said convexing comprises convexing said LAA wall portion by applying suction from a suction tube on said LAA wall portion, and wherein said grasping comprises grasping said convexed LAA portion using a tissue grasper that applies a force on a small area of said convexed LAA wall portion.

8. A method according to claim 1, wherein said grasping comprises tightening a loop around said convexed LAA wall portion.

9. A method according to claim 8, wherein said tightening comprises reversibly tightening said loop around said convexed LAA wall portion, and wherein said method comprises releasing said loop from said convexed LAA after said LAA is invaginated into said LA.

10. A tissue grasper comprising:

an elongated tubular body having a proximal end and a distal end, wherein said proximal end is connected to a vacuum source;

a collapsible distal suction cup coupled to said distal end, defining a distal opening and an internal lumen, wherein said collapsible distal suction cup is configured to apply vacuum from said vacuum source through said distal opening on a LAA wall with a force sufficient to convex a portion of said LAA wall into said lumen, and to controllably collapse on said convexed portion of the LAA with a force sufficient to hold said convexed portion in said lumen;

wherein said collapsible distal cup comprises a plurality of spaced-apart extensions movably coupled to said elongated tubular body and arranged on a circumference of the elongated tubular body distal end, wherein in an open expanded state of said collapsible distal cup said plurality of spaced-apart extensions are tilted outwardly, and wherein in a collapsed state of said collapsible distal cup, said plurality of spaced-apart extensions move inwardly and press against said convexed portion of said LAA with a force sufficient to hold said convexed LAA portion in said lumen;

wherein at least some of said plurality of spaced-apart extensions are interconnected by at least one wire, wherein application of force on said wire controllably move said collapsible distal cup between said open expanded state and said collapsed state, by moving said at least some of said plurality of spaced-apart extensions.

11. A tissue grasper according to claim 10, comprises one or more layers of sheet material interconnecting said plurality of spaced-apart extensions to form an enclosed lumen of said collapsible distal cup.

12. A tissue grasper according to claim 11, wherein said one or more layers of sheet material comprise an elastic sheet material.

13. A tissue grasper according to claim 10, wherein said collapsible distal suction cup comprises a distal leading edge configured to contact said LAA wall, and wherein said distal leading edge is covered with a smooth foldable fabric material configured to form a tight interface between said distal edge and said LAA wall.

14. A system for LAA closure comprising:

at least one tissue grasper according to claim 10 and one or more of, at least one ligator configured to pass within said catheter, to extend from said catheter distal opening, and to close said LAA and/or a LAA isolator configured to cover a LAA opening within the LA, to prevent flow of particles, debris and/or blood clots from said LAA into said LA.

* * * * *